United States Patent
Kapelewski et al.

(10) Patent No.: US 11,390,814 B2
(45) Date of Patent: Jul. 19, 2022

(54) CATALYTIC CONVERSION OF ALCOHOLS AND/OR ETHERS TO OLEFINS

(71) Applicant: ExxonMobil Technology and Engineering Company, Annandale, NJ (US)

(72) Inventors: Matthew T. Kapelewski, Flemington, NJ (US); Lei Zhang, Basking Ridge, NJ (US); Brandon J. O'Neill, Lebanon, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 0 days.

(21) Appl. No.: 17/060,126

(22) Filed: Oct. 1, 2020

(65) Prior Publication Data

US 2022/0106529 A1    Apr. 7, 2022

(51) Int. Cl.
*C10G 3/00* (2006.01)
*B01J 38/04* (2006.01)
*B01J 29/70* (2006.01)

(52) U.S. Cl.
CPC ............ *C10G 3/49* (2013.01); *B01J 29/708* (2013.01); *B01J 38/04* (2013.01); *C10G 2300/4018* (2013.01); *C10G 2400/20* (2013.01); *C10G 2400/22* (2013.01)

(58) Field of Classification Search
None
See application file for complete search history.

(56) References Cited

U.S. PATENT DOCUMENTS

| | | | | |
|---|---|---|---|---|
| 4,476,338 A | * | 10/1984 | Chang | C10G 3/49 |
| | | | | 585/322 |
| 2013/0217943 A1 | * | 8/2013 | Minoux | C07C 11/04 |
| | | | | 585/640 |
| 2013/0225894 A1 | * | 8/2013 | Chewter | C07C 1/20 |
| | | | | 585/640 |
| 2018/0201843 A1 | * | 7/2018 | O'Neill | B01J 37/28 |

FOREIGN PATENT DOCUMENTS

WO    WO-2009092779 A2  *  7/2009  ............ C08F 10/06

OTHER PUBLICATIONS

Ilias et al., "Mechanism of the Catalytic Conversion of Methanol to Hydrocarbons", ACS Catal. 2013, 3, 18-31.
Johansson et al., "The Hydrocarbon Pool in Ethanol-to-Gasoline over HZSM-5 Catalysts", Catalysis Letters 2009, 127, 1-6.
Narula et al., "Heterobimetallic Zeolite, InV-ZSM-5, Enables Efficient Conversion of Biomass Derived Ethanol to Renewable Hydrocarbons", Scientific Reports 2015, 5, 1-9.

* cited by examiner

*Primary Examiner* — In Suk C Bullock
*Assistant Examiner* — Alyssa L Cepluch
(74) *Attorney, Agent, or Firm* — Kristina Okafor

(57) ABSTRACT

Processes for the catalytic conversion of alcohols and/or ethers to olefins over zeolite catalysts are described. ZSM-48 and metal containing variants, such as Zn ZSM-48, produce high yields of olefins, particularly ethylene or C3+ olefins, between 200 and 500° C.

25 Claims, 15 Drawing Sheets

CATALYTIC CONVERSION OF ALCOHOLS AND/OR ETHERS TO OLEFINS

FIELD OF THE INVENTION

This disclosure relates to catalytic conversion of alcohols and/or ethers to olefins over zeolite based conversion catalysts. In particular the disclosure relates to catalytic conversion of alcohols and/or ethers over zeolite based conversion catalysts with high yields to ethylene or C3+ olefins.

BACKGROUND OF THE INVENTION

Conversion of methanol to olefins and other unsaturated compounds is a commonly used reaction scheme for chemical manufacture. Conventional methods can involve exposing a methanol-containing feed to a molecular sieve, such as ZSM-5 or SAPO-34.

Alcohols, especially those produced from biological sources, are potential alternatives to petroleum-based fuels. For example, ethanol can be derived from the fermentation of biological feedstocks, as well as the bio-conversion of waste streams from steel manufacturing and of municipal solid waste. As ethanol is not a drop-in replacement for gasoline or diesel, however, it must be further upgraded to be used as a fuel in most applications.

Narula C. K. et al (Scientific Reports volume 5, Article number: 16039, 2015) describe the conversion of ethanol to olefins over an InV-ZSM-5 zeolite. The catalyst converts ethanol at 360° C. to 6.5% olefins, 33.2% paraffins, and 60.2% aromatics.

In view of the foregoing, it would be desirable to provide improved catalysts and processes for the conversion of oxygenates such as alcohols or ethers to olefins.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY OF THE INVENTION

The present disclosure relates to novel processes for converting alcohols and/or ethers to olefins.

In one aspect the present disclosure provides a process for converting alcohols and/or ethers to olefins, said process comprising:
contacting a feed comprising one or more alcohols and/or one or more ethers with a conversion catalyst in a reaction zone at a temperature from about 200° C. to about 550° C. under conditions effective to produce an olefin-containing effluent, the olefin-containing effluent comprising 40 wt. % or more of olefins and 30 wt. % or less of aromatics relative to a weight of hydrocarbons in the olefin-containing effluent, the conversion catalyst comprising a zeolite framework structure.

In embodiments, the wt. % of olefins relative to the weight of hydrocarbons in the olefin-containing effluent is 45 wt. % or more, or 50 wt. % or more, or 55 wt. % or more, or 60 wt. % or more, or 65 wt. % or more, or 70 wt. % or more, or 75 wt. % or more, or 80 wt. % or more, or 85 wt. % or more.

In embodiments, the wt. % of aromatics relative to the weight of hydrocarbons in the olefin-containing effluent is 20 wt. % or less, or 15 wt. % or less, or 10 wt. % or less, or 5 wt. % or less.

In embodiments, the wt. % of C3+ olefins relative to the weight of hydrocarbons in the olefin-containing effluent is 5 wt. % or more, or 10 wt. % or more, or 15 wt. % or more, or 20 wt. % or more, or 25 wt. % or more, or 30 wt. % or more, or 35 wt. % or more.

In embodiments, the wt. % of C4+ olefins relative to the weight of hydrocarbons in the olefin-containing effluent is 5 wt. % or more, or 10 wt. % or more, or 15 wt. % or more, or 20 wt. % or more, or 25 wt. % or more, or 30 wt. % or more, or 35 wt. % or more.

In embodiments, the wt. % of paraffins relative to the weight of hydrocarbons in the olefin-containing effluent is 45 wt. % or less, or 40 wt. % or less, or 35 wt. % or less, or 30 wt. % or less, or 25 wt. % or less, or 20 wt. % or less, or 15 wt. % or less, or 10 wt. % or less.

In embodiments, the wt. % of ethylene relative to the weight of hydrocarbons in the olefin-containing effluent is 50 wt. % or more, or 60 wt. % or more, or 70 wt. % or more, or 80 wt. % or more, or 90 wt. % or more, or 95 wt. % or more.

In some embodiments, the contacting occurs from about 250° C. to about 500° C., or from about 300° C. to about 500° C.

In some embodiments, the contacting occurs at a pressure from about 10 psig to about 400 psig, or from about 10 psig to about 100 psig.

In some embodiments, the WHSV is from about 0.1 $h^{-1}$ to about 10 $h^{-1}$, or from about 0.5 $h^{-1}$ to about 5 $h^{-1}$.

In embodiments, the conversion catalyst comprises an MRE type zeolite.

In some embodiments, the conversion catalyst comprises ZSM-48.

In other embodiments, the conversion catalyst comprises silicalite.

In some embodiments, the conversion catalyst comprises a self-bound zeolite.

In alternate embodiments, the conversion catalyst further comprises about 1 wt. % to about 40 wt. % of a binder, for example a binder comprising one or more of $Al_2O_3$, $TiO_2$, $ZrO_2$, $SiO_2$, $SiO_2/Al_2O_3$, and MgO, based on the total weight of the conversion catalyst.

In embodiments, the conversion catalyst further comprises about 0.1 wt. % to about 20 wt. % of one or more metals selected from groups 1 to 14 of the periodic table.

In embodiments, the conversion catalyst further comprises about 0.1 wt. % to about 20 wt. % of one or more metals selected from groups 12 to 14 of the periodic table.

In embodiments, the conversion catalyst further comprises about 0.1% to about 5 wt. % of one or more metals selected from groups 12 to 14 of the periodic table.

In embodiments, the conversion catalyst further comprises about 0.1 wt. % to about 20 wt. % of one or more metals selected from groups 1 or 2 of the periodic table.

In embodiments, the conversion catalyst further comprises about 0.1% to about 5 wt. % of one or more metals selected from groups 1 or 2 of the periodic table.

In embodiments, the one or more metals comprise one or more of Zn, Ga, B, Ca, Ti, V, Fe, Cu, Mo, Ru, Pd, Rh, Ir, Nb, W, Re, and Pt.

In embodiments, the conversion catalyst comprises Zn. In some embodiments, the conversion catalyst comprises about 0.1 wt. % to about 2 wt. % Zn.

In embodiments, the reaction zone comprises one or more of a fixed bed reactor, a fluidized bed reactor, a riser reactor, and a moving bed reactor. Preferred reactors include a moving bed reactor or a fixed bed reactor.

A feature of the present disclosure is that as a conversion catalyst is exposed to increasing amounts of alcohol and/or ether containing feed, the relative yields of products in the olefin-containing effluent may change. Without wishing to be bound by theory this is likely due to a build up of carbonaceous material in the conversion catalyst.

As certain desirable products may have high yields only after being exposed to a particular amount of alcohol and/or ether containing feed, operating the reaction zone so that it comprises conversion catalyst which has been exposed to a particular amount of feed advantageously may lead to high yields of desirable products. This may be achieved through catalyst regeneration strategies which regulate the average conversion catalyst exposure to alcohol and/or ether.

In other words, the observation that relative product yields may change with time on stream may be advantageously utilized to control or maximize the yield of particular products, for example C3+ olefins or ethylene.

In embodiments, wherein the reaction zone comprises a moving bed reactor, the process further comprises a step of transferring at least a portion of the conversion catalyst to a regeneration zone, separate from the reaction zone, and contacting the conversion catalyst with a regeneration gas in the regeneration zone to at least partially remove coke deposited on the conversion catalyst in the reaction zone, whereby the conversion catalyst is at least partially regenerated, and then returning the thus at least partially regenerated conversion catalyst to the reaction zone.

In some embodiments, the at least partially regenerated conversion catalyst is returned to the reaction zone at a rate sufficient to produce an olefin-containing effluent comprising 5 wt. % or more of C3+ olefins, relative the weight of hydrocarbons in the olefin-containing effluent The at least partially regenerated conversion catalyst may be returned to the reaction zone at a rate sufficient to produce an olefin-containing effluent comprising 10 wt. % or more of C3+ olefins, or 15 wt. % or more, or 20 wt. % or more, or 25 wt. % or more, or 30 wt. % or more, or 35 wt. % or more, relative the weight of hydrocarbons in the olefin-containing effluent.

In additional or alternate embodiments, the at least partially regenerated conversion catalyst is returned to the reaction zone at a rate sufficient such that 1 gram of conversion catalyst is, on average, exposed to at least 200 gram of feed in the reaction zone.

The at least partially regenerated conversion catalyst may be returned to the reaction zone at a rate sufficient such that 1 gram of conversion catalyst is, on average, exposed to at least 300 gram of feed, or at least 400 gram of feed, or at least 500 gram of feed in the reaction zone.

In additional or alternate embodiments, the at least partially regenerated conversion catalyst is returned to the reaction zone at a rate sufficient such that 1 gram of conversion catalyst is, on average, exposed to no more than 200 gram of feed in the reaction zone.

The at least partially regenerated conversion catalyst may be returned to the reaction zone at a rate sufficient such that 1 gram of conversion catalyst is, on average, exposed to no more than 150 gram of feed, or no more than 100 gram of feed, or no more than 50 gram of feed in the reaction zone.

In additional or alternate embodiments, the at least partially regenerated conversion catalyst is returned to the reaction zone at a rate sufficient to afford an average degree of conversion catalyst coking within the reaction zone to produce an olefin-containing effluent comprising 5 wt. % or more of C3+ olefins, relative the weight of hydrocarbons in the olefin-containing effluent.

The at least partially regenerated conversion catalyst may be returned to the reaction zone at a rate sufficient to afford an average degree of conversion catalyst coking within the reaction zone to produce an olefin-containing effluent comprising 10 wt. % or more of C3+ olefins, or 15 wt. % or more, or 20 wt. % or more, or 25 wt. % or more, or 30 wt. % or more, or 35 wt. % or more relative the weight of hydrocarbons in the olefin-containing effluent.

In additional or alternate embodiments, the at least partially regenerated conversion catalyst is returned to the reaction zone at a rate sufficient to produce an olefin-containing effluent comprising 50 wt. % or more of ethylene, relative the weight of hydrocarbons in the olefin-containing effluent The at least partially regenerated conversion catalyst may be returned to the reaction zone at a rate sufficient to produce an olefin-containing effluent comprising 60 wt. % or more of ethylene, or 70 wt. % or more, or 80 wt. % or more, or 90 wt. % or more, or 95 wt. % or more, relative the weight of hydrocarbons in the olefin-containing effluent.

In additional or alternate embodiments, the at least partially regenerated conversion catalyst is returned to the reaction zone at a rate sufficient to afford an average degree of conversion catalyst coking within the reaction zone to produce an olefin-containing effluent comprising 50 wt. % or more of ethylene, relative the weight of hydrocarbons in the olefin-containing effluent.

The at least partially regenerated conversion catalyst may be returned to the reaction zone at a rate sufficient to afford an average degree of conversion catalyst coking within the reaction zone to produce an olefin-containing effluent comprising 60 wt. % or more of ethylene, or 70 wt. % or more, or 80 wt. % or more, or 90 wt. % or more, or 95 wt. % or more, relative the weight of hydrocarbons in the olefin-containing effluent.

In embodiments, the regeneration gas comprises oxygen. In some embodiments, the regeneration gas may be air.

In embodiments, the regeneration zone comprises one or more of a riser reactor, a moving bed reactor or a fixed bed reactor.

In embodiments, the one or more alcohols comprise one or more of ethanol, 1-propanol, 2-propanol, 1-butanol and 2-butanol.

In embodiments, the one or more alcohols may be derived from fermentation or bio-conversion. In alternate or additional embodiments, the one or more alcohols may be derived from the conversion of synthesis gas.

In embodiments, the one or more alcohols may further comprise water.

In embodiments, the feed comprising one or more alcohols comprises at least 5% by weight of the one or more alcohols.

In embodiments the one or more ethers comprise one or more of diethyl ether, di-n-propyl ether, di-iso-propyl ether, di-n-butyl ether and di-iso-butyl ether.

In some embodiments, the process further comprises the step of separating water from the olefin-containing effluent.

In some embodiments, the process further comprises the step of separating at least some of the olefin-containing effluent to provide a stream rich in olefins.

In some embodiments, the process further comprises the step of separating at least some of the stream rich in olefins to provide at least a stream rich in ethylene and a stream rich in C3+ olefins.

In some embodiments, the stream rich in ethylene is further processed, for example, oligomerized to higher olefins.

In some embodiments, at least some of the C3+ olefins are oligomerized to higher olefins, and, optionally, further hydrogenated to jet or diesel fuels.

Advantages of the processes disclosed herein may include one or more of the following:
- high alcohol and/or ether conversion;
- high yields of olefins including high yields of C3+ or C4+ olefins;
- ability to select operating conditions through the use of, for example, moving bed reactors to maximise or control the yields of particular products.

Further features and advantages of the present disclosure will be understood by reference to the following drawings and detailed description.

DETAILED DESCRIPTION OF THE EMBODIMENTS

Figure 1:
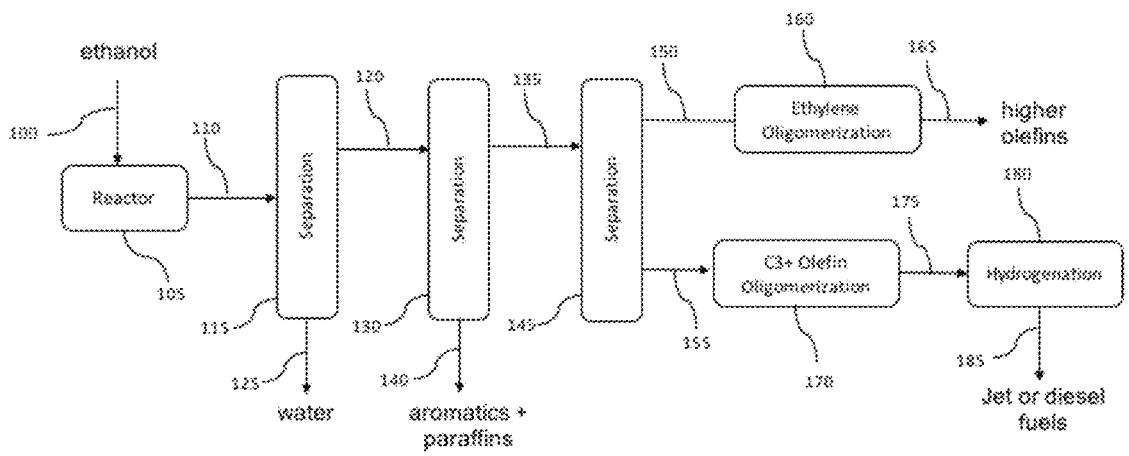
FIG. 1 is flowsheet showing a process according to an embodiment of the present disclosure.

The following is a detailed description of the disclosure provided to aid those skilled in the art in practicing the present disclosure. Those of ordinary skill in the art may make modifications and variations in the embodiments described herein without departing from the spirit or scope of the present disclosure.

Although any processes and materials similar or equivalent to those described herein can also be used in the practice or testing of the present disclosure, the preferred processes and materials are now described.

It must also be noted that, as used in the specification and the appended claims, the singular forms 'a', 'an' and 'the' include plural referents unless otherwise specified. Thus, for example, reference to 'olefin' may include more than one olefins, and the like.

Throughout this specification, use of the terms 'comprises' or 'comprising' or grammatical variations thereon shall be taken to specify the presence of stated features, integers, steps or components but does not preclude the presence or addition of one or more other features, integers, steps, components or groups thereof not specifically mentioned.

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

Unless specifically stated or obvious from context, as used herein, the term "about" is understood as within a range of normal tolerance in the art, for example within two standard deviations of the mean. 'About' can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term 'about'.

Any processes provided herein can be combined with one or more of any of the other processes provided herein.

Ranges provided herein are understood to be shorthand for all of the values, including non-integer values, within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein the term 'moving bed' reactor means a zone or vessel with contacting of solids and gas flows such that the superficial gas velocity (U) is below the velocity required for dilute-phase pneumatic conveying of solid particles in order to maintain a solids bed with void fraction below 95%. A moving-bed reactor may operate under several flow regimes including settling or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$). As used herein '$U_{mf}$' is the minimum fluidization velocity, '$U_{mb}$' is the minimum bubbling velocity, '$U_c$' is the onset velocity for the transition to turbulent fluidization, and '$U_{tr}$' is the transport velocity. These different fluidization regimes have been described in, for example, Kunii, D., Levenspiel, O., Chapter 3 of Fluidization Engineering, 2" Edition, Butterworth-Heinemann, Boston, 1991.

As used herein the term 'fluidized bed' reactor means a zone or vessel with contacting of solids and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%. Minimum fluidization velocity is discussed in, for example, the Kunii publication noted above.

As used herein the term 'riser reactor' means a zone or vessel (such as a vertical cylindrical pipe) used for net upwards transport of solids in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in the Kunii publication noted above.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims.

Overview

The present disclosure describes the use of zeolites, such as ZSM-48, for the conversion of alcohols and/or ethers to olefins, especially C3+ olefins, which can be subsequently upgraded to gasoline and diesel through oligomerization. ZSM-48 produces a significant amount of C3+ olefins during the conversion of, for example, ethanol, which are particularly suitable for subsequent upgrading to high value gasoline and diesel-range molecules. ZSM-48 may produce 60-95% olefins, depending on the conditions of operation, with 20-30% C3+ olefins being produced at 350° C.

The present disclosure further describes the use of a metal containing zeolite, 0.5% Zn/ZSM-48, for the conversion of alcohols and/or ethers to olefins. These olefins can be upgraded through an MTG (methanol to gasoline)-type process to gasoline or diesel fuel molecules through oligomerization of olefins.

0.5% Zn/ZSM-48 demonstrates about 100% conversion of ethanol with a >95% selectivity to olefins at 350 and 450° C. Of these olefins, 60-80% are ethylene at 350° C., while 70-95% are ethylene at 450° C. Conditions could likely be further optimized (potentially to lower temperatures) to maintain high ethanol conversion while increasing selectivity for C3+ olefins. Conversely, ethanol dehydration to ethylene is facile at higher temperatures, leading to the potential to use this catalyst for ethylene production from ethanol as required.

Ethanol, especially that produced from biological sources, is a potential alternative to petroleum-based fuels. Ethanol can be derived from the fermentation of biological feedstocks, as well as the bio-conversion of waste streams from steel manufacturing and of municipal solid waste. As ethanol is not a drop-in replacement for gasoline or diesel, however, it must be further upgraded to be used as a fuel in most applications. Conversion of ethanol is advantaged if it can be run at more dilute concentrations, obviating the need to purify ethanol via energetically-costly multi-stage distillation.

The present disclosure further describes ZSM-48 as a catalyst for the conversion of 40% ethanol to olefins, which can be subsequently upgraded to gasoline and diesel through oligomerization. ZSM-48 produces a significant amount of C3+ olefins during the conversion, which are particularly suitable for subsequent upgrading to high value gasoline and diesel-range molecules through an olefin to distillate (OTD) process. ZSM-48 initially produces ~25% C3+ olefins, with further time on stream resulting in the production of primarily ethylene. However, this is quite significant, as the ability to control the product slate through the use of a moving bed reactor may enable product yield control, leading to constant high C3+ olefin production from ethanol over ZSM-48.

In various embodiments, a conversion catalyst comprising a suitable zeotype framework material (such as a zeolitic material) can be used for conversion of alcohols and/or ethers to olefins. In some embodiments, an optionally metal-enhanced zeotype conversion catalyst, such as a conversion catalyst including a Zn-enhanced zeotype framework material, may be used for the conversion of alcohols and/or ethers to olefins.

As used herein, a zeotype refers to a crystalline material having a porous framework structure built from tetrahedral atoms connected by bridging oxygen atoms. Examples of known zeotype/zeolite frameworks are given in the "Atlas of Zeolite Frameworks" published on behalf of the Structure Commission of the International Zeolite Association", 6th revised edition, Ch. Baerlocher, L. B. McCusker, D. H. Olson, eds., Elsevier, New York (2007) and the corresponding web site, http://www.iza-structure.org/databases/. Under this definition, a zeolite can refer to aluminosilicates having a zeotype framework type as well, while a zeotype more generally refers crystalline structures having a suitable framework structure that may contain oxides of Si, Al, and/or heteroatoms different from Si and Al. Such heteroatoms can include any heteroatom generally known to be suitable for inclusion in a zeotype framework, such as gallium, boron, germanium, phosphorus, zinc, and/or other transition metals that can substitute for silicon and/or aluminum in a zeotype framework.

As used herein, a Cx hydrocarbon, alcohol, olefin, oxygenate, or other compound, or of a carbon chain in such a compound, is a reference to a compound (or carbon chain in such a compound) that contains the specified number of carbons. Ethanol is an example of a C2 alcohol. C3+ is an example of one or more chemical compounds, for example one or more olefins, having three or more carbon atoms. A reference to a stream or fraction containing Cx-Cy compounds corresponds to a stream or fraction that contains at least one component having a carbon backbone with x carbons, y carbons, or a number of carbons between x and y. For example, a stream containing C3-C6 olefins corresponds to a stream containing at least one of C3 olefins, C4 olefins, C5 olefins, or C6 olefins.

Feedstocks and Products

In various embodiments, conversion catalysts described herein can be used for conversion of alcohol and/or ether containing feeds to olefins. In embodiments, the feeds may comprise one or more alcohols, one or more ethers or one or more alcohols and one or more ethers. In some embodiments the alcohols may comprise one or more of ethanol, 1-propanol, 2-propanol, 1-butanol and 2-butanol. In some embodiments, the ethers may comprise one or more of diethyl ether, di-n-propyl ether, di-iso-propyl ether, di-n-butyl ether and di-iso-butyl ether.

Preferably an ethanol containing feed can include 3 wt. % or more of ethanol, or 5 wt. % or more of ethanol, or 10 wt. % or more of ethanol, or 20 wt. % or more of ethanol, or 30 wt. % or more of ethanol, or 40 wt. % or more of ethanol, or 50 wt. % or more of ethanol, or 75 wt. % or more of ethanol, or 90 wt. % or more of ethanol, or at least 95 wt. % of ethanol. The ethanol may be derived from any convenient source. The ethanol may be produced from biological sources, such as by fermentation or bio-conversion.

In addition to alcohols and/or ethers, a feed can also include diluents, such as water (in liquid or gaseous form), nitrogen or other inert gases, and/or paraffins or other non-reactive hydrocarbons. Optionally, at least a portion of such diluents can be removed prior to exposing the alcohol to a conversion catalyst. Optionally, the feed can further include olefins, such as 10 wt. % or less of olefins, or 5 wt. % or less. Such optional olefins can, for example, correspond to C2-C6 olefins, such as having 70 wt. % or more of the olefins correspond to C2-C3 olefins, or such as having 50 wt. % or more of the olefins correspond to C3-C6 olefins. In such optional aspects, 10 wt. % or less of the olefins can correspond to C7+ olefins, or 5 wt. % or less, or 1 wt. % or less.

In various embodiments, alcohols and ethers may be converted into olefins in the presence of a conversion catalyst under conversion conditions The conversion catalyst may comprise a zeolite (or other zeotype) in its original crystalline form or after formulation into catalyst extrudates, such as by extrusion.

In some embodiments the catalyst particles are self-bound catalyst particles. The term "self-bound" means that the conversion catalyst is free of any binder, for example inorganic oxide binders, such as one or more of $Al_2O_3$, $TiO_2$, $ZrO_2$, $SiO_2$, $SiO_2/Al_2O_3$, and MgO, frequently combined with zeolite catalysts to enhance their physical properties.

One example of binding zeolite crystals to form catalyst particles is to form a self-bound catalyst. A process for producing zeolite extrudates in the absence of a binder is disclosed in, for example, U.S. Pat. No. 4,582,815, the entire contents of which are incorporated herein by reference.

As an alternative to forming self-bound catalysts, zeolite crystals can be combined with a binder, such as, for example, one or more of $Al_2O_3$, $TiO_2$, $ZrO_2$, $SiO_2$, $SiO_2/Al_2O_3$, and MgO to form bound catalysts. Generally, a binder can be present in an amount between about 1 wt. % and about 90 wt. %, for example between about 3 wt. % and about 90 wt. % of a catalyst, about 3 wt. % to about 80 wt. %, about 5 wt. % to about 90 wt. %, about 5 wt. % to about 80 wt. %, about 5 wt. % to about 40 wt. %, or about 10 wt. % to about 40 wt. %. In some embodiments, the catalyst can include at least about 5 wt. % binder, for example at least about 10 wt. %, or at least about 20 wt. %. Additionally, or alternately, the catalyst can include about 90 wt. % or less of binder, for example about 80 wt. % or less, about 50 wt. % or less, about 40 wt. % or less, or about 35 wt. % or less. Combining the zeolite and the binder can generally be achieved, for example, by mulling a mixture of the zeolite and binder (optionally an aqueous mixture) and then extruding the mixture into catalyst pellets.

In some embodiments, a binder for formulating a catalyst can be selected so that the resulting bound catalyst has a micropore surface area of at least about 290 $m^2/g$, for example at least about 300 $m^2/g$ or at least about 310 $m^2/g$. Optionally but preferably, a suitable binder can be a binder with a surface area of about 200 $m^2/g$ or less, for example about 175 $m^2/g$ or less or about 150 $m^2/g$ or less. Unless otherwise specified, the surface area of the binder is defined herein as the combined micropore surface area and mesopore surface area of the binder.

The zeolite employed in the present conversion catalyst generally comprises at least one medium pore aluminosilicate zeolite having a Constraint index of 1-12 (as defined in U.S. Pat. No. 4,016,218). Suitable zeolites include zeolites having an MFI or MEL framework, such as ZSM-5 or ZSM-11. ZSM-5 is described in detail in U.S. Pat. No. 3,702,886 and RE29,948. ZSM-11 is described in detail in U.S. Pat. No. 3,709,979. Preferably, the zeolite is ZSM-5. Other useful zeolites can include ZSM-12 (U.S. Pat. No. 3,832,449); ZSM-22 (U.S. Pat. No. 4,556,477); ZSM-23 (U.S. Pat. No. 4,076,842); ZSM-34 (U.S. Pat. No. 4,079,095) ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). Non-limiting examples of SAPO and AlPO molecular sieves can include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, and AlPO-46.

Another option for characterizing a zeolite or other molecular sieve is based on the nature of the ring channels in the zeolite. The ring channels in a zeolite can be defined based on the number of atoms including in the ring structure that forms the channel. In some embodiments, a zeolite can include at least one ring channel based on a 10-member ring. In such aspects, the zeolite preferably does not have any ring channels based on a ring larger than a 10-member ring. Examples of suitable framework structures having a 10-member ring channel but not having a larger size ring channel include EUO, FER, IMF, LAU, MEL, MFI, MFS, MTT, MWW, NES, PON, SFG, STF, STI, TON, TUN, MRE, and PON framework types.

In some alternative embodiments, the zeolite can be a molecular sieve that includes an 8-member ring channel (small pore molecular sieves), a 10-member ring channel (as described above), or a 12-member ring channel (large pore molecular sieves), but does not have any ring channels based on a ring larger than a 12-member ring. In such aspects, suitable large pore molecular sieves can include those having AFI, AFS, ATO, ATS, *BEA, BEC, BOG, BPH, CAN, CON, EMT, EON, EZT, FAU, GME, GON, IFR, ISV, -*ITN, IWR, IWW, LTL, MAZ, MEI, MOR, MOZ, MSE, MTW, OFF, OKO, OSI, SAF, SAO, SEW, SFE, SFO, SSF, SSY, and USI framework types. In such aspects, suitable small pore molecular sieves can include those having the AEI, AFT, AFX, ATT, DDR, EAB, EPI, ERI, KFI, LEV, LTA, MER, MON, MTF, PAU, PHI, RHO, and SFW framework types.

Generally, a zeolite having the desired activity can have a silicon to aluminum molar ratio of about 10 to about 300, for example about 15 to about 100, about 20 to about 80, or about 20 to about 40. In some embodiments, the silicon to aluminum ratio can be at least about 10, for example at least about 20, at least about 30, at least about 40, at least about 50, or at least about 60. Additionally, or alternatively, the silicon to aluminum ratio can be about 300 or less, for example about 200 or less, about 100 or less, about 80 or less, about 60 or less, or about 50 or less.

In some preferred embodiments, the silicon to aluminum ratio can be at least about 20, for example at least about 30 or at least about 40. In such embodiments, the silicon to aluminum ratio can optionally be about 100 or less, for example about 80 or less, about 60 or less, about 50 or less, or about 40 or less. Typically, reducing the silicon to aluminum ratio in a zeolite can result in a zeolite with a higher acidity, and therefore higher activity for cracking of hydrocarbon or hydrocarbonaceous feeds, such as petroleum feeds. With respect to conversion of alcohols and/or ethers to olefins, such increased cracking activity due to a decrease in the silicon to aluminum ratio may result in increased formation of residual carbon or coke during the conversion reaction. Such residual carbon can deposit on the zeolite conversion catalyst, leading to a change in the properties of the catalyst over time. Having a silicon to aluminum ratio of at least about 40, for example at least about 50 or at least about 60, can reduce/minimize the amount of additional residual carbon formed due to the acidic or cracking activity of the conversion catalyst.

It is noted that the molar ratio described herein is a ratio of silicon to aluminum. If a corresponding ratio of silica to alumina were described, the corresponding ratio of silica ($SiO_2$) to alumina ($Al_2O_3$) would be twice as large, due to the presence of two aluminum atoms in each alumina stoichiometric unit compare to only one silicon atom in the silica stoichiometric unit. Thus, a silicon to aluminum ratio of 10 corresponds to a silica to alumina ratio of 20.

In some optional aspects, the zeolite conversion catalyst employed herein can further be characterized by at least one or at least two of the following properties: (a) a mesoporosity of greater than about 20 $m^2/g$, for example greater than about 30 $m^2/g$, and less than about 150 $m^2/g$, for example less than about 145 $m^2/g$; (b) a microporous surface area of at least about 140 $m^2/g$, for example at least about 145 $m^2/g$.

Additionally, or alternatively, a conversion catalyst may have a combined micropore and mesopore surface area of at least about 30 $m^2/g$, for example at least about 50 $m^2/g$.

Of these properties, mesoporosity can be determined by several factors for a given zeolite, including the crystal size of the zeolite. Microporous surface area is determined by the pore size of the zeolite and the availability of the zeolite pores at the surfaces of the catalyst particles. Producing a zeolite conversion catalyst with the desired minimum mesoporosity and microporous surface area should be well within the expertise of anyone of ordinary skill in zeolite chemistry. It is noted that mesopore or external surface area and micropore surface area can be characterized, for example, using adsorption-desorption isotherm techniques within the expertise of one of skill in the art, such as the BET (Brunauer Emmett Teller) method.

It is noted that the micropore surface area can be characterized for either zeolite crystals or a catalyst formed from the zeolite crystals. In various aspects, the micropore surface area of a self-bound catalyst or a catalyst formulated with a separate binder can be at least about 290 $m^2/g$, for example at least about 300 $m^2/g$, at least about 310 $m^2/g$, at least about 320 $m^2/g$, or at least about 330 $m^2/g$. Typically, a formulation of zeolite crystals into catalyst particles (either self-bound or with a separate binder) can result in some loss of micropore surface area relative to the micropore surface area of the zeolite crystals. Thus, to provide a catalyst having the desired micropore surface area, the zeolite crystals can also have a micropore surface area of at least about 290 $m^2/g$, for example at least about 300 $m^2/g$, or at least about 310 $m^2/g$. As a practical matter, the micropore surface area of a zeolite crystal and/or a corresponding self-bound or bound catalyst as described herein can be less than about 1000 $m^2/g$, and typically less than about 750 $m^2/g$. Additionally or alternatively, the micropore surface area of a catalyst (self-bound or with a separate binder) can be about 105% or less of the micropore surface area of the zeolite crystals in the catalyst, and typically about 100% or less of the micropore surface area of the zeolite crystals in the catalyst, for example from about 80% to 100% of the micropore surface area of the zeolite crystals in the catalyst. In some embodiments, the micropore surface area of a catalyst can be at least about 80% of the micropore surface area of the zeolite crystals in the catalyst, for example at least about 85%, at least about 90%, at least about 95%, at least about 97%, or at least about 98%, and/or about 100% or less, for example about 99% or less, about 98% or less, about 97% or less, or about 95% or less.

When used in the present conversion catalyst, the zeolite can be present at least partly in the hydrogen (active) form. Depending on the conditions used to synthesize the zeolite, this may correspond to converting the zeolite from, for example, the sodium form. This can readily be achieved, for example, by ion exchange to convert the zeolite to the ammonium form followed by calcination in air or an inert atmosphere at a temperature of about 400° C. to about 700° C. to convert the ammonium form to the active hydrogen form. Alternatively, methods for directly converting a sodium form zeolite to a hydrogen form zeolite can also be used. Such methods are well known to the person of ordinary skill in the art.

Additionally, or alternatively, the conversion catalyst can include and/or be enhanced by one or more metals selected from groups 1 to 14 of the periodic table.

The metal can be incorporated into the zeolite by any convenient method known in the art, such as by impregnation or by ion exchange. After impregnation or ion exchange, the metal-enhanced catalyst may be treated in air or an inert atmosphere at a temperature of about 400° C. to about 700° C. The amount of metal can be related to the molar amount of aluminum present in the zeolite. In some embodiments, the molar amount of the metal can correspond to about 0.1 to about 1.3 times the molar amount of aluminum in the zeolite. In some embodiments, the molar amount of metal can be at least about 0.1 times the molar amount of aluminum in the zeolite, for example at least about 0.2 times, at least about 0.3 times, or at least about 0.4 times. Additionally, or alternatively, the molar amount of metal can be about 1.3 times or less relative to the molar amount of aluminum in the zeolite, for example about 1.2 times or less, about 1.0 times or less, or about 0.8 times or less. Still further additionally or alternately, the amount of metal can be expressed as a weight percentage of the conversion catalyst, such as having at least about 0.1 wt. % of metal, at least about 0.25 wt. %, at least about 0.5 wt. %, at least about 0.75 wt. %, or at least about 1.0 wt. %. Additionally, or alternatively, the amount of metal can be about 20 wt. % or less, for example about 10 wt. % or less, about 5 wt. % or less, about 2.0 wt. % or less, about 1.5 wt. % or less, about 1.2 wt. % or less, about 1.1 wt. % or less, or about 1.0 wt. % or less.

In some embodiments, the conversion catalyst can include one or more metals from groups 12 to 14 of the periodic table and thus include the metal zinc. In additional or alternate embodiments, the conversion catalyst can include one or more metals from groups 1 and 2 of the periodic table. The total weight of the metals can be about 0.1 wt. % to about 10.0 wt. % based on the total weight of the conversion catalyst. Thus, the upper limit on the range of metals in the conversion catalyst may be 10.0 wt. %, 9.0 wt. %, 8.0 wt. %, 7.0 wt. %, 6.0 wt. %, 5.0 wt. %, 4.0 wt. %, 3.0 wt. %, 2.0 wt. %, or 1.0 wt. %; and the lower limit on the range may be 9.0 wt. %, 8.0 wt. %, 7.0 wt. %, 6.0 wt. %, 5.0 wt. %, 4.0 wt. %, 3.0 wt. %, 2.0 wt. %, 1.0 wt. %, or 0.1 wt. %. Ranges expressly disclosed include combinations of any of the above-enumerated upper and lower limits, e.g., 0.1 to 10.0 wt. %, 0.1 to 8.0 wt. %, 0.1 to 6.0 wt. %, 0.1 to 5.0 wt. %, 0.1 to 4.0 wt. %, 0.1 to 3.0 wt. %, 0.1 to 2.0 wt. %, 0.1 to 1.0 wt. %, 1.0 to 10.0 wt. %, 1.0 to 9.0 wt. %, 1.0 to 8.0 wt. %, 1.0 to 7.0 wt. %, 1.0 to 6.0 wt. %, 1.0 to 5.0 wt. %, 1.0 to 4.0 wt. %, 1.0 to 3.0 wt. %, etc.

To form a metal-enhanced conversion catalyst, a self-bound (or bound) catalyst can, for example, be impregnated via incipient wetness with a solution containing the desired metal for impregnation, such as one or more of Zn, Ga, B, Ca, Ti, V, Fe, Cu, Mo, Ru, Pd, Rh, Ir, Nb, W, Re, and Pt. The impregnated catalyst can then be dried overnight at about 120° C., followed by calcination in air for about 3 hours at about 540° C. More generally, a transition metal can be incorporated into the zeolite crystals and/or catalyst at any convenient time, such as before or after ion exchange to form H-zeolite crystals, or before or after formation of an extrudate. In some embodiments that are preferred from a standpoint of facilitating manufacture of a zeolite catalyst, the transition metal can be incorporated into the catalyst (such as by impregnation or ion exchange) after formation of the catalyst by extrusion or another convenient method.

The yield of olefins relative to the total hydrocarbons in the ethanol conversion product may be 5 wt. % to 95 wt. %, or 10 wt. % to 95 wt. %, or 15 wt. % to 90 wt. %, or 20 wt. % to 90 wt. %, or 30 wt. % to 90 wt. %, or 40 wt. % to 90 wt. %, or 20 wt. % to 80 wt. %, or 30 wt. % to 80 wt. %, or 20 wt. % to 70 wt. %, or 20 wt. % to 60 wt. %, or 20 wt. % to 50 wt. %.

Additionally, or alternatively, the yield of aromatics relative to the total hydrocarbons in the conversion product may be 0.1 wt. % to 50 wt. %, 0.5 wt. % to 40 wt. %, or 1 wt. % to 30 wt. %, or 1 wt. % to 20 wt. % or 1 wt. % to 10 wt. % or 1 wt. % to 5 wt. %.

Additionally, or alternatively, the yield of paraffins relative to the total hydrocarbon product may be 5 wt. % to 50 wt. %, or 5 wt. % to 40 wt. %, or 5 wt. % to 30 wt. % or 5 wt. % to 20 wt. % or 10 wt. % to 40 wt. % or 10 wt. % to 30 wt. %

Additionally, or alternatively, the yield of C3+ olefins relative to the total hydrocarbon product may be 5 wt. % or more, or 10 wt. % or more, or 15 wt. % or more, or 20 wt. % or more, or 25 wt. % or more, or 30 wt. % or more, or 35 wt. % or more.

Additionally, or alternatively, the yield of C4+ olefins relative to the total hydrocarbon product may be 5 wt. % or more, or 10 wt. % or more, or 15 wt. % or more, or 20 wt. % or more, or 25 wt. % or more, or 30 wt. % or more, or 35 wt. % or more.

Additionally, or alternatively, the yield of ethylene relative to the total hydrocarbon product may be 50 wt. % or more, or 60 wt. % or more, or 70 wt. % or more, or 80 wt. % or more, or 90 wt. % or more, or 95 wt. % or more.

In the claims below, the relative amounts of paraffins, olefins, and aromatics in a sample can be determined based on ASTM D6839.

Suitable and/or effective conditions for performing a conversion reaction may include average reaction temperatures of 200° C. to 550° C. (or 250° C. to 550° C., or 300° C. to 550° C., or 350° C. to 550° C., or 400° C. to 500° C.), total pressures between 10 psig (~70 kPa-g) to 400 psig (~2700 kPa-g), or 50 psig (~350 kPa-g) to 350 psig (~2400 kPa-g), or 100 psig (~700 kPa-g) to 300 psig (~2100 kPa-g), and an alcohol space velocity between 0.1 $h^{-1}$ to 10 $h^{-1}$ based on weight of alcohol relative to weight of catalyst. For example, the average reaction temperature may be at least 200° C., or at least 250° C., or at least 300° C., or at least 350° C., or at least 400° C., or at least 450° C. Additionally or alternately, the average reaction temperature can be 550° C. or less, or 500° C. or less, or 450° C. or less, or 400° C. or less. In this specification, average reaction temperature is defined as the average of the temperature at the reactor inlet and the temperature at the reactor outlet for the reactor where the conversion reaction is performed. In some embodiments, where lower pressures are used, the pressure can correspond to 70 kPa-g to 700 kPa-g. As another example, the total pressure can be at least 70 kPa-g, or at least 350 kPa-g, or at least 500 kPa-g, or at least 700 kPa-g, or at least 1000 kPa-g. Additionally or alternately, the total pressure can be 3000 kPa-g or less, or 2700 kPa-g or less, or 2400 kPa-g or less, or 2100 kPa-g or less.

Various types of reactors may provide a suitable configuration for performing a conversion reaction. Suitable reactors may include fixed bed reactors, moving bed reactors, fluidized bed reactors, and riser reactors.

It is noted that the activity and/or selectivity of the herein disclosed conversion catalysts for alcohol and/or ether conversion may vary as the conversion catalysts are exposed to increasing amounts of alcohol and/or ether feed. The variation may occur, for example, because of build-up of coke in the conversion catalyst. In some embodiments, a feature of the presently disclosed processes is that the average residence time of conversion catalyst in a reaction zone may be controlled through withdrawal of at least some of the conversion catalyst from the reaction zone, regeneration of the conversion catalyst in a regeneration zone, and return of the regenerated conversion catalyst to the reaction zone. The average residence time may be selected to control conversion catalyst activity, alcohol and/or ether conversion and product selectivity so as to maximize yields of particular products.

In embodiments where a conversion catalyst can be removed from the reaction zone for regeneration and recycle during operation in a reactor, such as a moving bed reactor, a fluidized bed reactor or a riser reactor, conversion catalyst can be removed, regenerated in a regeneration zone and the regenerated conversion catalyst returned to the reaction zone.

The regeneration zone may be a reactor operated as a fixed bed, a fluidized bed, an ebulating bed, a settling bed, a riser reactor or a combination thereof. In practice, the regeneration zone may include a plurality of reactors, such as a plurality of riser reactors connected in parallel. The regeneration zone should be operated at the minimum temperature required to remove the required amount of coke at the design residence time and in particular the temperature should not exceed the point at which metal oxide volatilization occurs or the conversion catalyst substrate undergoes rapid deterioration. Typically, regeneration zone temperature is from about 400° C. to about 700° C., such as from about 550° C. to about 650° C. Catalyst residence time in the regeneration zone also should be minimized to reduce catalyst aging rate and maximize percent of time the catalyst spends in the reactor doing useful work. In embodiments, the average residence time of catalyst particles in the regeneration zone may be between 0.1 and 100 minutes, or between 1 and 20 minutes.

In some embodiments, the alcohol feed and/or conversion reaction environment can include water in various proportions. Conversion of alcohol to olefins results in production of water as a product, so the relative amounts of alcohol and water can vary within the reaction environment.

While only conventional separation schemes are likely required in the herein disclosed processes (e.g. distillation, adsorption with molecular sieves, liquid-liquid extraction), the person of ordinary skill in the art would appreciate that these separations may be performed in a multitude of ways depending on how the process is designed.

In the present disclosure, reference to 'separation' of process streams may refer to one or more distillative separations, wherein components are separated based on boiling point or adsorption with molecular sieves/membrane based on size or polarity.

FIG. 1 illustrates a proposed process scheme for ethanol conversion to olefins over an ethanol conversion catalyst as disclosed herein. Feed stream 100, comprising ethanol, is fed to reactor 105 which contains an olefin conversion catalyst. The effluent 110 which comprises olefins is fed to separator 115 which removes water as stream 125 and provides hydrocarbon stream 120. The hydrocarbon stream is fed to further separator 130 which separates the hydrocarbons into olefin rich stream 135 and stream 140 which contains aromatics and paraffins. The olefin rich stream is sent to further separator 145 which separates the heavier C3+ olefins 155 from ethylene 150. The ethylene may be sent to oligomerization reactor 160 to provide higher olefin stream 165. The C3+ olefins may be oligomerized in oligomerization unit 170 to afford higher olefins which may be fed via 175 to hydrogenator 180 to yield stream 185 comprising jet or diesel fuels.

In separator 115 about 39.1 wt. % of products that are water (based on the mass content of the hydroxyl group plus a proton from ethanol) are separated from the hydrocarbons.

EXAMPLES

The ZSM-48 used in the herein disclosed processes was a bound ZSM-48 comprising 80:20 ZSM-48:Catapal™ 200. Catapal 200 is an alumina hydrate available from Sasol Performance Chemicals.

Example 1: Preparation of 0.5% Zn ZSM-48

About 20 g of ZSM-48 extrudate was measured for its water absorption factor which was determined to be about 0.62. 0.46 g of $Zn(NO_3)_2$ $6H_2O$ was added to 11.94 g $H_2O$. The resulting solution was slowly added to the ZSM-48 in a pill coater set to 30 rpm by slowly spraying in the Zn solution over 5 min. The resulting extrudate was mixed for 20 min at 10 rpm, held at ambient temperature for 1 h, and then dried in an oven at 175° C. overnight. The extrudate was further dried in flowing dry air at 500° C. for 3 h, producing 18.8 g total 0.5% Zn ZSM-48.

Example 2: Conversion of Ethanol to Olefins with ZSM-48

Ethanol conversion experiments were performed in a ~10 cc reactor, with a fixed bed of ~2 g zeolite catalyst diluted in sand. The ethanol was 100% ethanol. The ethanol feed rate was 5 cc/h for all experiments, and pressure was varied during the runs are described below. The WHSV for all experiments was ~2.

ZSM-48 catalyst was contacted with ethanol in the fixed bed reactor operating at 350° C. or 450° C. and at a pressure of about 15 psig. The ethanol was fed to the zeolite catalyst bed and the effluent from the reactor periodically analyzed for product composition. Ethanol conversion was ~100% throughout the runs.

Gas phase analysis was performed with an online GC. The liquid products were separated by density into aqueous and hydrocarbon components. The aqueous phase was analyzed by density measurement and the hydrocarbon phase was analyzed by GC.

Figure 2:
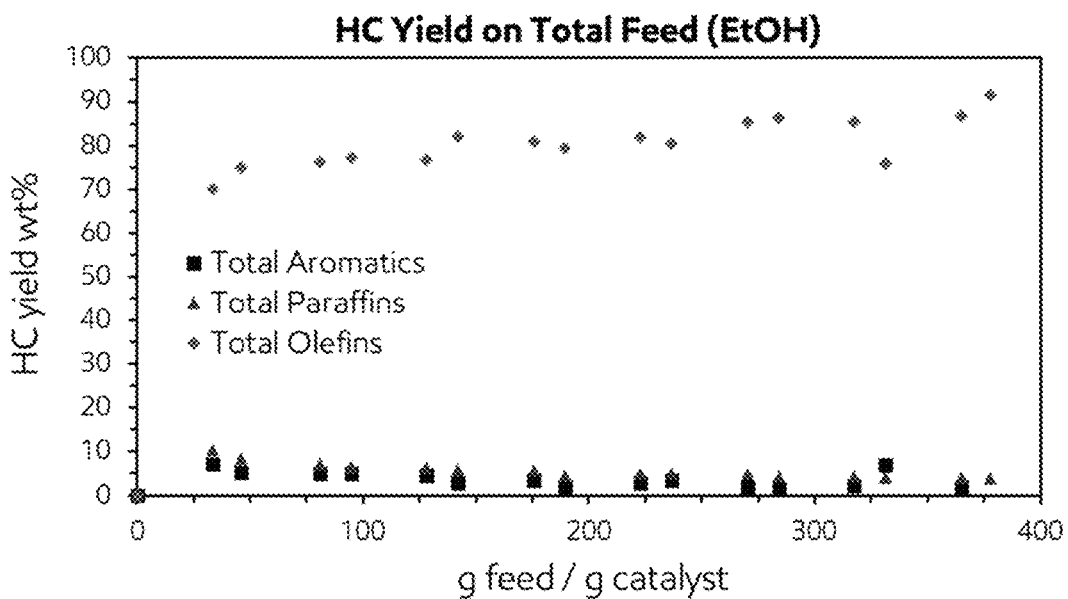
FIG. 2 is a graph showing total hydrocarbon (HC) yields for aromatics, paraffins, and olefins over ZSM-48 at 350° C.
Figure 3:
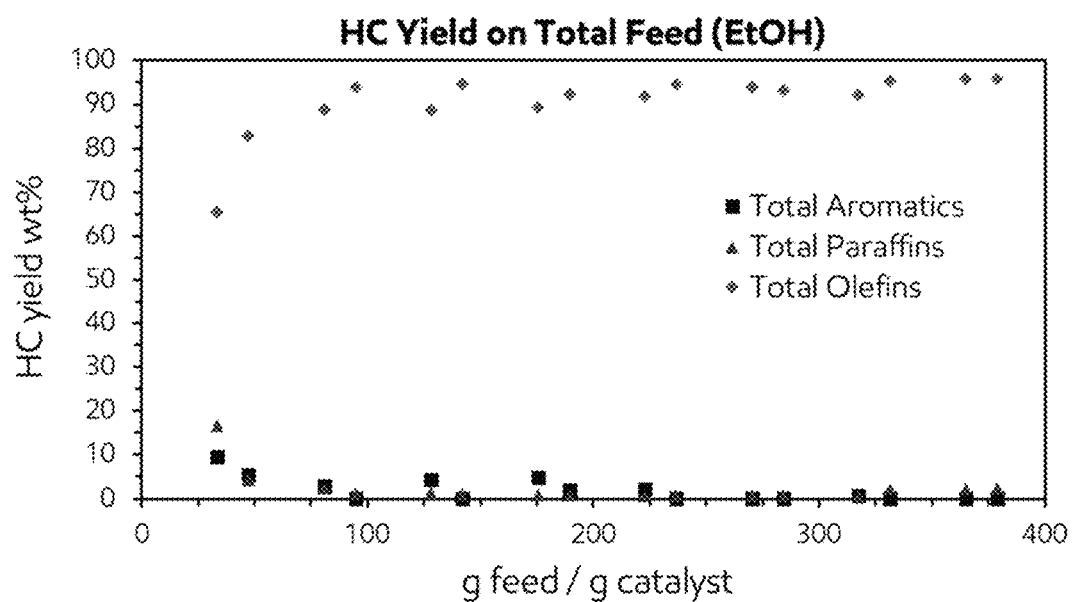
FIG. 3 is a graph showing total hydrocarbon (HC) yields for aromatics, paraffins, and olefins over ZSM-48 at 450° C.

FIGS. 2 and 3 illustrate the weight % hydrocarbon yield against gram ethanol feed per gram catalyst at 350° C. and 450° C. respectively.

Referring to FIG. 2, initially, olefins comprise 70% of the hydrocarbon products, with this rising to 90% at around 375 g feed/g catalyst.

These data highlight the ability of ZSM-48, as a structure with 1D channels and 10 membered rings, to inhibit the cyclization required to form aromatics and remain within the olefin methylation cycle. It is notable that this was possible despite the C2 starting unit in ethanol, which could potentially ethylate olefins and more quickly produce larger olefins more prone to cyclization. However, the inhibition of the cyclic transition state likely holds and olefins were observed as the primary products.

At the higher 450° C. temperature (FIG. 3), the production of olefins was even more pronounced, with olefin yield rapidly increasing to >90 wt. % and remaining there for the duration of the experiment. This is significant, as the higher temperature would perhaps be expected to favor higher aromatics production than at 350° C., as the hydrogen transfer reaction required to dehydrogenate naphthenes to aromatics is more likely at higher temperature. However, the opposite was observed, which is possibly a result of the combination of the inhibition of ring formation in the first place by the small, 1D channels of ZSM-48, coupled with the more active cracking of higher olefins to lighter olefins at the higher temperature.

Figure 4:
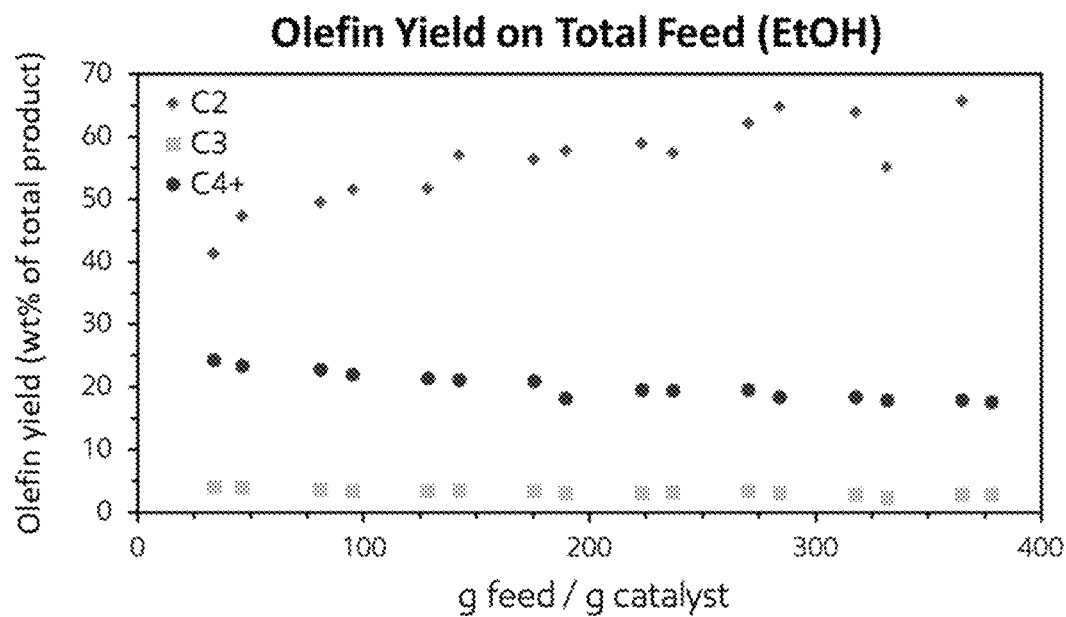
FIG. 4 is a graph showing olefin yields as a percent of the total hydrocarbon product for ZSM-48 at 350° C.
Figure 5:
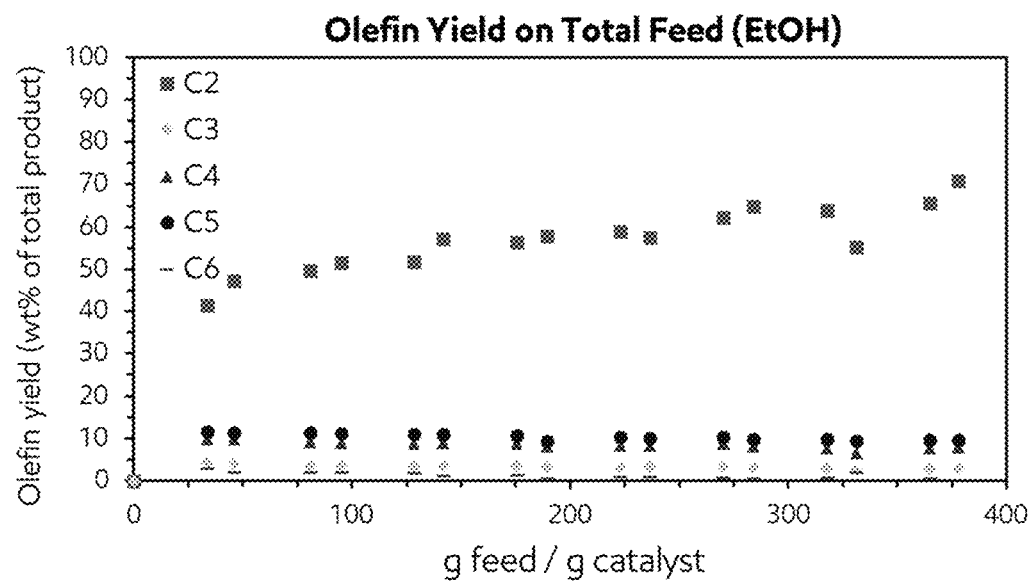
FIG. 5 is a graph showing further breakdown of olefin yields as a percent of the total hydrocarbon product for ZSM-48 at 350° C.
Figure 6:
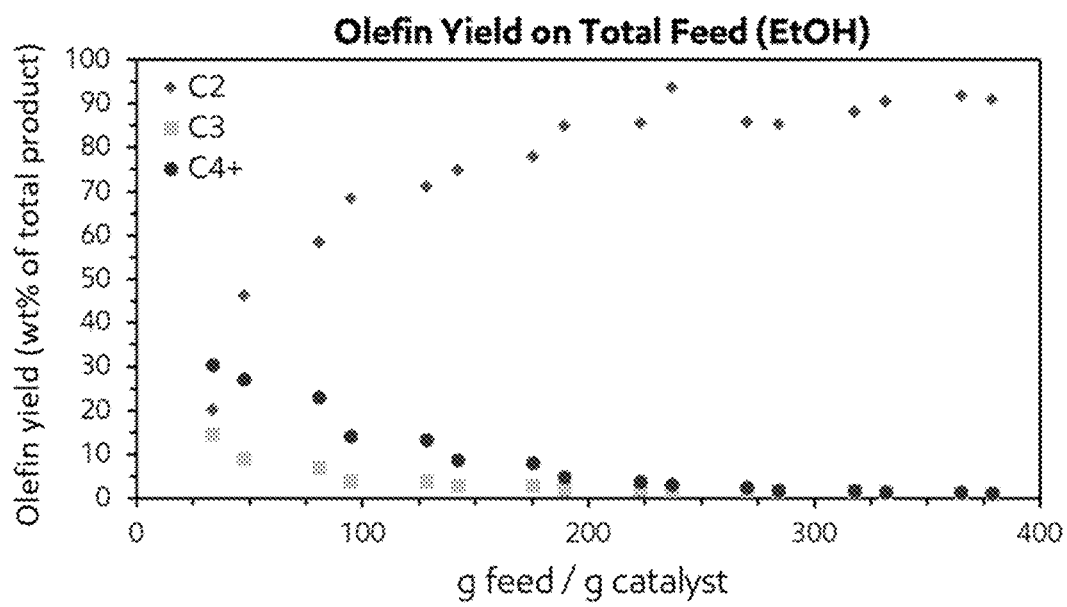
FIG. 6 is a graph showing olefin yields as a percent of the total hydrocarbon product for ZSM-48 at 450° C.

The olefin distribution using ZSM-48 is depicted in FIGS. 4, 5 and 6. Referring first to FIG. 4 (350° C.), ethylene was the primarily olefinic product, accounting for 40-65 wt. % of the total hydrocarbon product. C4+ olefins made up 20-25 wt. % of the hydrocarbon products and propylene was <5 wt. %. This distribution is interesting as ethanol dehydration to ethylene appeared to be fast, compared to the methylation/ethylation of ethylene to higher olefins, indicated by the high ethylene production. However, some alkylation of ethylene did occur to produce higher olefins, indicating the possibility that cracking of higher olefins, which was likely fast relative to ring-closing to form naphthenes and aromatics, leading to a substantial portion of the ethylene as well. This is suggested through a further breakdown of the olefin production by carbon number (FIG. 5), which shows higher selectivity to C5 olefins over C4 olefins.

The cracking required to produce the C1 unit necessary for methylation to the odd numbered species indicates this is occurring in the system, which likely contributes to the higher production of C5 over C4 olefins. However, this mechanism would be expected to yield C3 olefins as well, of which there are very few in the products.

Olefin yields at 450° C. are illustrated in FIG. 6. This was quite different from 350° C. during the initial stages of the reaction and C4+ olefins were the primary product at slightly more than 30 wt. % of the hydrocarbon products, with an additional 15 wt. % propylene. The higher temperature in this reaction likely better enabled the alkylation of olefins, leading to a higher production of C3+ olefins.

Interestingly, C5 olefins are more prevalent in the products than C4 olefins suggesting that cracking of higher olefins is occurring in order to produce significant quantities of olefins with an odd number of carbons. It has been proposed that the production of propylene stems from cracking of higher olefins, possibly 4-methyl-1-pentene. However, as the reaction progressed and the catalyst began to coke, ethylene again became the dominant product, eventually reaching 85 wt. % of the hydrocarbon product stream.

As a point of comparison, an experiment with methanol (450° C., 15 psig, similar ZSM-48 catalyst) produced a maximum of ~55-60% olefins. Ethanol feed produced significantly higher total olefins products of 60-90 wt. %, depending on time on stream. Additionally, the distribution of olefins was different. With methanol, the C2, C3, and C4+ olefin distribution was (all values are wt. % of total product): 4.7, 22.0, 27.8, respectively. This differs from the comparable olefin distribution of ~42, 4.5, and 25%, respectively, with ethanol, in that the higher olefin production was primarily driven by a large increase in ethylene production that more than offset the decrease in propylene production. This is likely driven by the C2 unit already present in ethanol. Overall, the total C4+ olefins production, which are the most readily oligomerized to distillate, was similar between methanol and ethanol feeds.

Utilizing the enabling technology of, for example, a moving bed reactor, the operating window can essentially be chosen, with the catalyst operating continuously at a specific level of coking. In this case, rapidly reactivating the ZSM-48 catalyst and operating at low coking levels may be optimal, as this allows for the greatest production of C3+ olefins useful for oligomerization to fuels.

In Table 1, the "optimal" conditions for producing olefins at each temperature are shown for ZSM-48. Given the potential to select operating conditions and an operating window with, for example, a moving bed reactor, these yields may be achieved in a commercial process. In Table 1, 'P'=paraffins, 'A'=aromatics and 'O'=olefins.

TABLE 1

| | ZSM-48 % product | |
|---|---|---|
| Temperature (° C.) | P/A/O | C3+ olefins |
| 350 | 10/7/70 | 29 |
| 450 | 17/10/66 | 45 |

Example 3: Conversion of Ethanol to Olefins with 0.5% Zn ZSM-48

A sample of ZSM-48 with 0.5% Zn by weight prepared as in Example 1, was tested to determine the extent to which metal loading impacts the conversion of ethanol to olefins.

Figure 7:
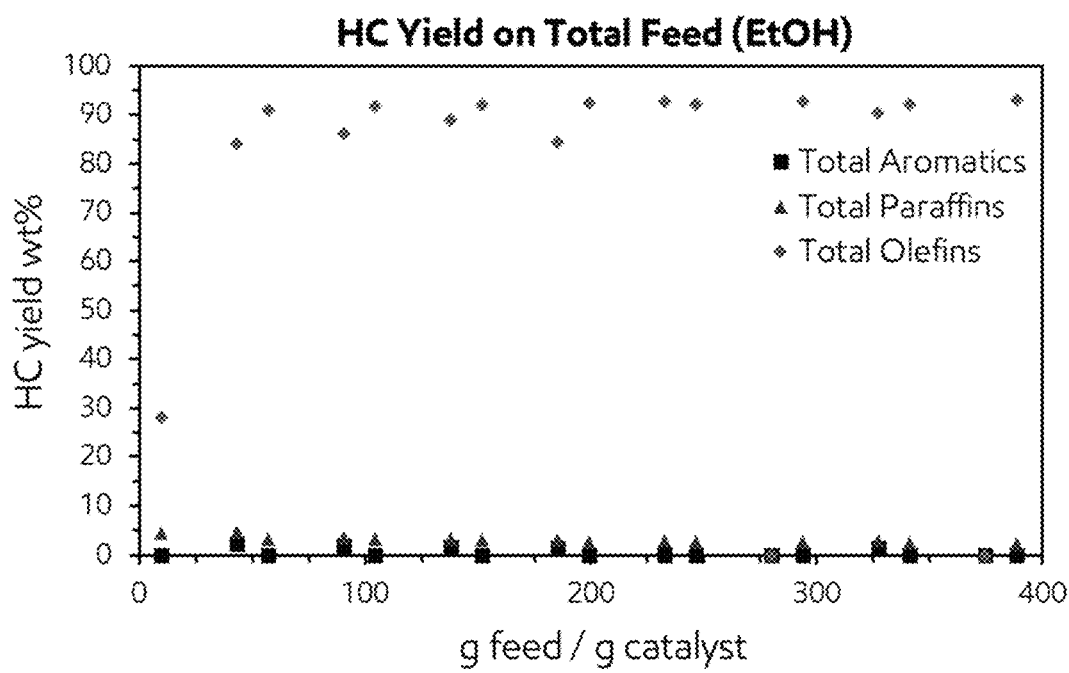
FIG. 7 is a graph showing total hydrocarbon (HC) yields for aromatics, paraffins, and olefins over 0.5% Zn/ZSM-48 at 350° C.
Figure 8:
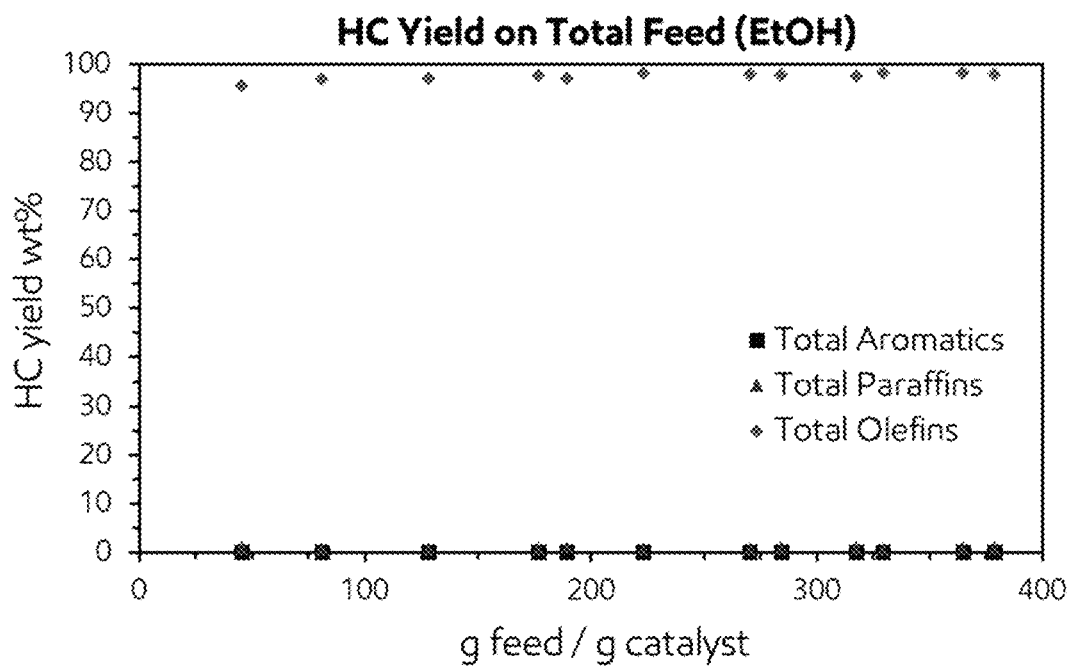
FIG. 8 is a graph showing total hydrocarbon (HC) yields for aromatics, paraffins, and olefins over 0.5% Zn/ZSM-48 at 450° C.

FIGS. 7 and 8 illustrate the weight % hydrocarbon yield against gram ethanol feed per gram catalyst at 350° C. and 450° C. respectively. The data indicate that 0.5% Zn ZSM-48 showed nearly exclusive production of olefins, especially at 450° C. This result is highly beneficial from the standpoint of wanting exclusively olefins to feed into a further olefin oligomerization step.

Figure 9:
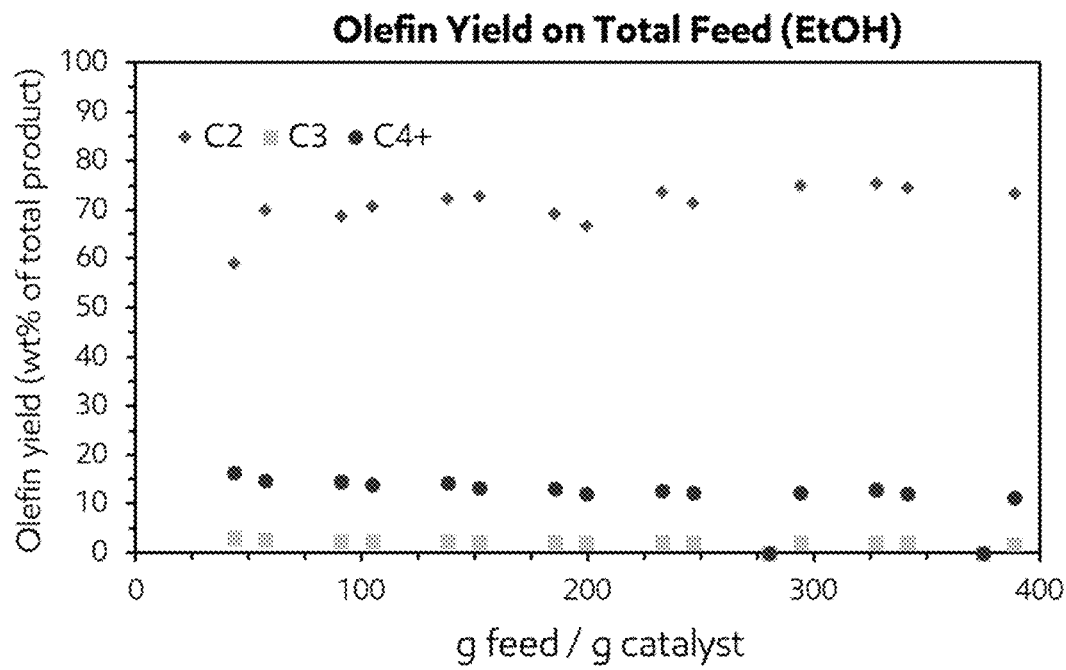
FIG. 9 is a graph showing olefin yields as a percent of the total hydrocarbon product for 0.5% Zn/ZSM-48 at 350° C.
Figure 10:
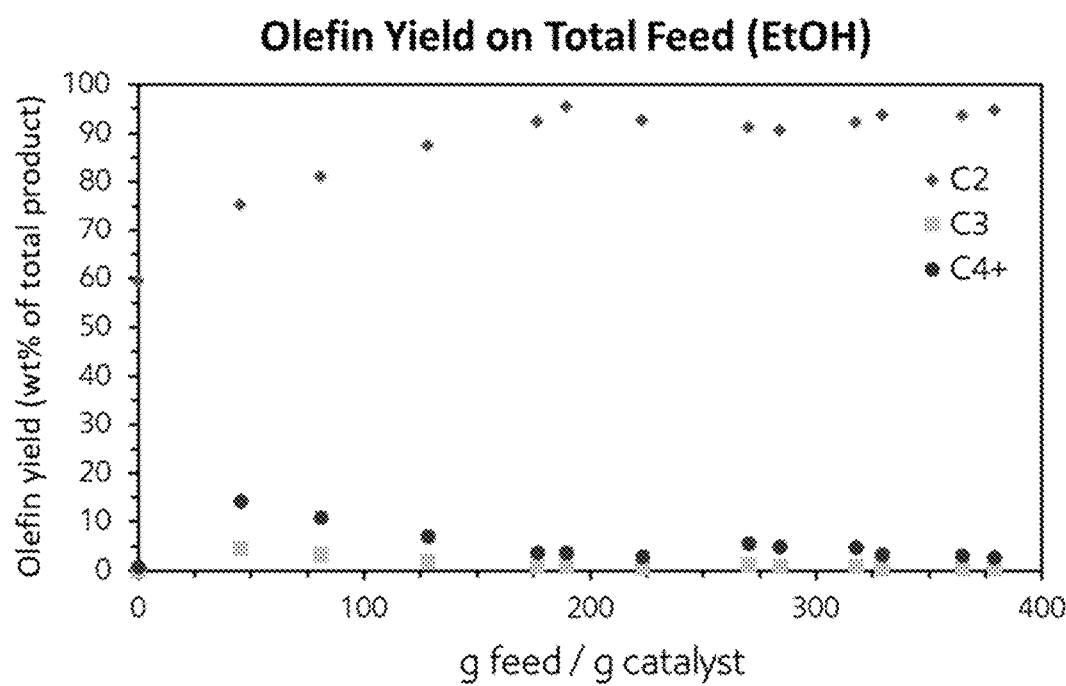
FIG. 10 is a graph showing olefin yields as a percent of the total hydrocarbon product for 0.5% Zn/ZSM-48 at 450° C.

Despite the higher selectivity to total olefins, the selectivity to C3+ olefins was significantly lower (FIGS. 9 and 10) than that for non-metallated ZSM-48. The included Zn possibly favors dehydration or blocks acid sites from facilitating chain growth that leads to higher olefins due to 1-D zeolite channels.

As a point of comparison, a similar ZSM-48 run with methanol (450° C., 15 psig, similar ZSM-48 catalyst) produced a maximum of ~62% olefins. The ethanol feed produced significantly higher total olefins products of 75-90 wt. %, depending on time on stream. Additionally, the distribution of olefins is different. With methanol feed, the C2, C3, and C4+ olefin distribution was (all values are wt. % of total product): 1.8, 21.2, 38.1, respectively. This differs from the comparable olefin distribution of ~76, 4.5, and 15%, respectively, with ethanol, in that the higher olefin production was primarily driven by a large increase in ethylene production that more than offset the decrease in propylene production. This is likely driven by the C2 unit already present in ethanol. Overall, the total C4+ olefins production, which are the most readily oligomerized to distillate, was advantaged for the methanol feed while ethylene production was advantaged for the ethanol feed.

In Table 2, the "optimal" conditions for producing olefins at each temperature are shown for 0.5% Zn/ZSM-48. Given the potential to select operating conditions and an operating window with, for example, a moving bed reactor, these yields may be achieved in a commercial process. In Table 2, 'P'=paraffins, 'A'=aromatics and 'O'=olefins.

TABLE 2

| | 0.5% Zn ZSM-48 % product | |
|---|---|---|
| Temperature (° C.) | P/A/O | C3+ olefins |
| 350 | 5/2/84 | 19 |
| 450 | 1/0/96 | 1 |

Example 4: Conversion of 40% Ethanol to Olefins with ZSM-48

ZSM-48 catalyst was tested with a feed of 40% ethanol in water. Results were collected at 300, 350, and 450° C. for the 40% ethanol feed.

Figure 11:
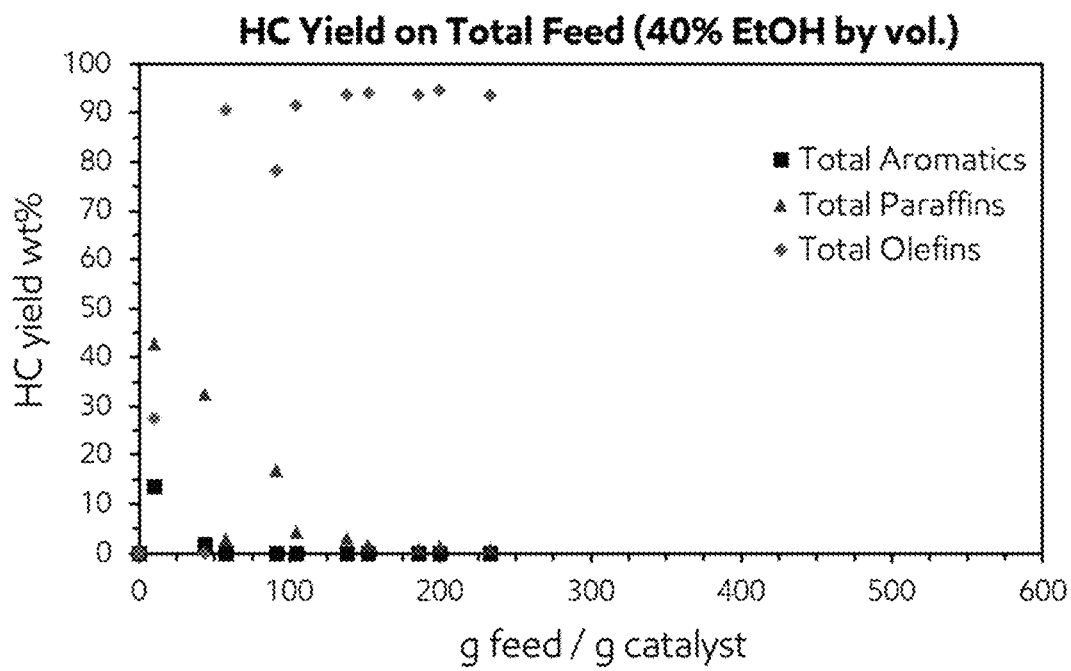
FIG. 11 is a graph showing total hydrocarbon (HC) yields for aromatics, paraffins, and olefins over ZSM-48 at 300° C. utilizing 40% ethanol feed.
Figure 12:
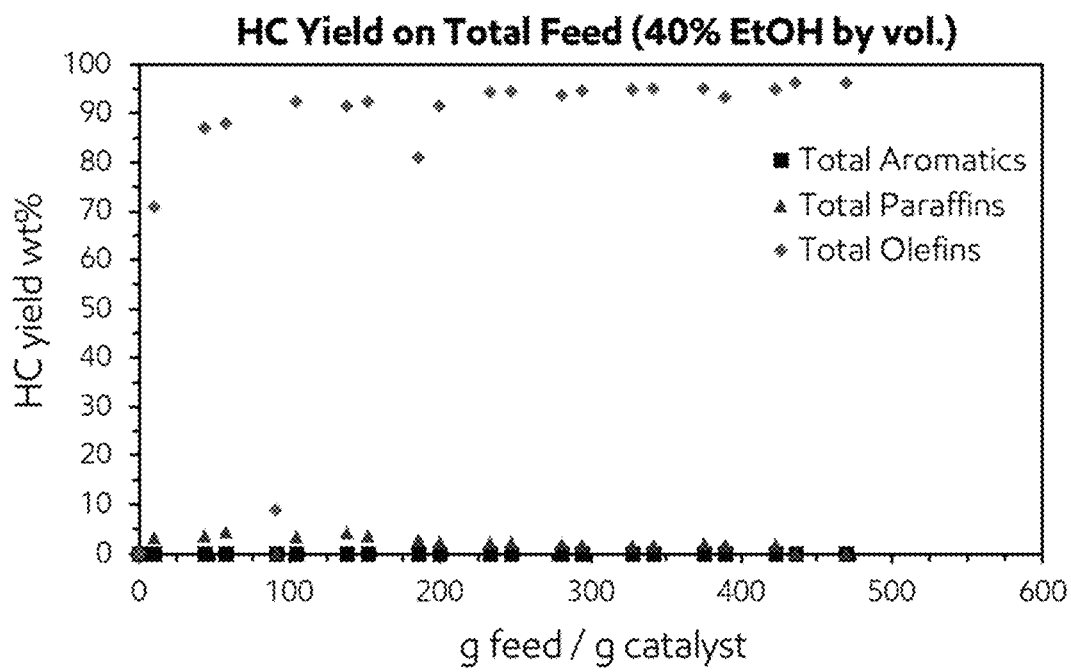
FIG. 12 is a graph showing total hydrocarbon (HC) yields for aromatics, paraffins, and olefins over ZSM-48 at 350° C. utilizing 40% ethanol feed.
Figure 13:
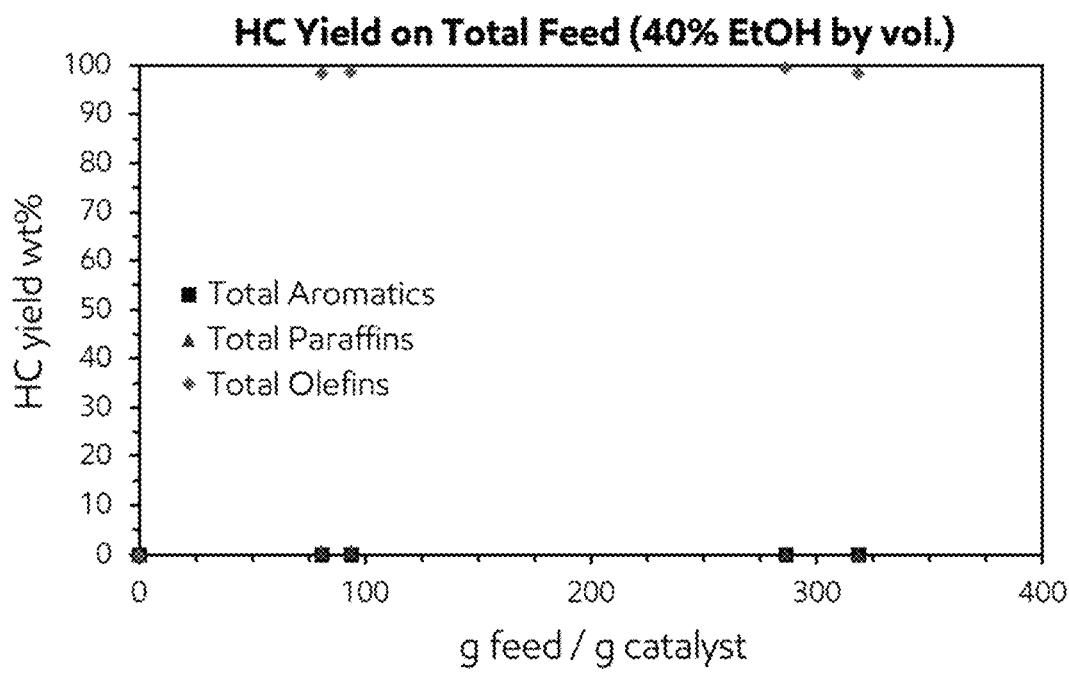
FIG. 13 is a graph showing total hydrocarbon (HC) yields for aromatics, paraffins, and olefins over ZSM-48 at 450° C. utilizing 40% ethanol feed.

Overall hydrocarbon yields are depicted in FIGS. 11-13 for the 300, 350, and 450° C. runs, respectively, all of which were conducted at 15 psig pressure for the duration of each run.

From FIG. 11, it is evident that ZSM-48 initially showed some conversion of the aqueous ethanol to paraffins and aromatics, but this rapidly decreased to almost exclusively olefins. This was likely the result of modification of the catalyst in the presence of water. Corresponding results for experiments at 350 and 450° C. (FIGS. 12 and 13) indicate that this modification was quite rapid, with high quantities of olefins being produced at all points during the runs. The 450° C. data suffered from some experimental issues, but the results can be inferred from the data points obtained, in which ~100% olefins were produced as hydrocarbon products.

Figure 14:
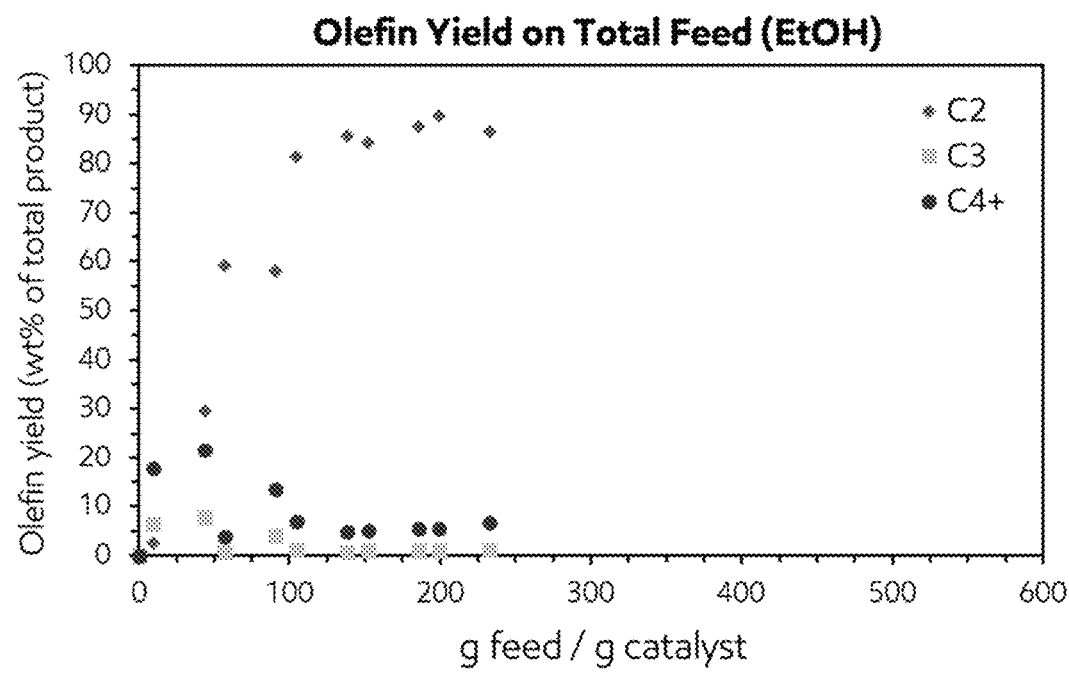
FIG. 14 is a graph showing olefin yields as a percent of the total hydrocarbon product for ZSM-48 at 300° C. utilizing 40% ethanol feed.
Figure 15:
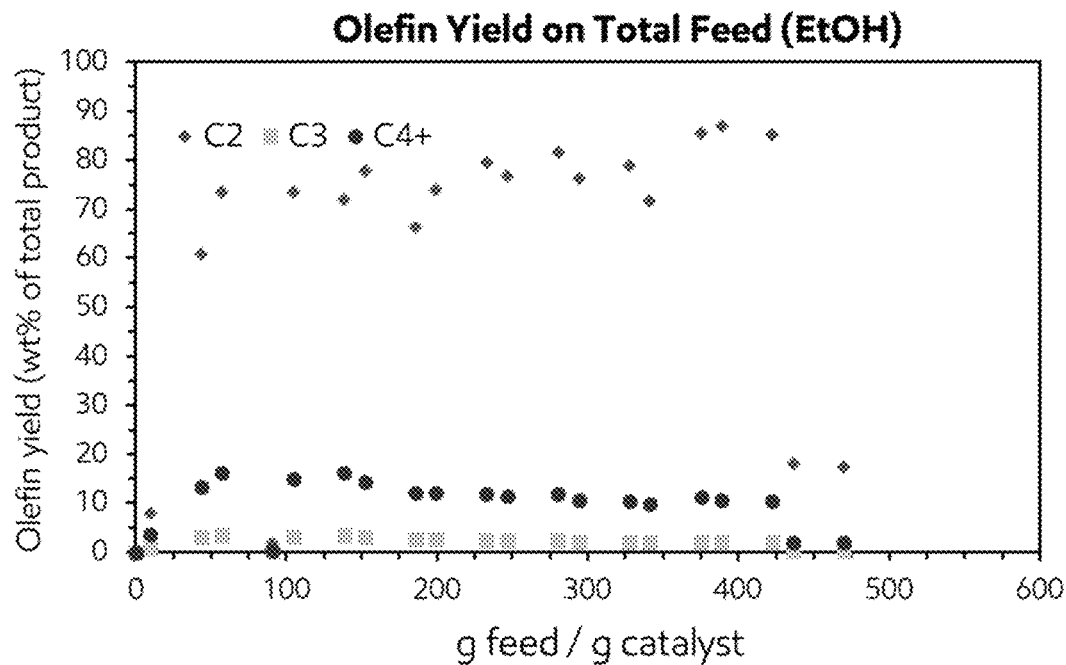
FIG. 15 is a graph showing olefin yields as a percent of the total hydrocarbon product for ZSM-48 at 350° C. utilizing 40% ethanol feed.
Figure 16:
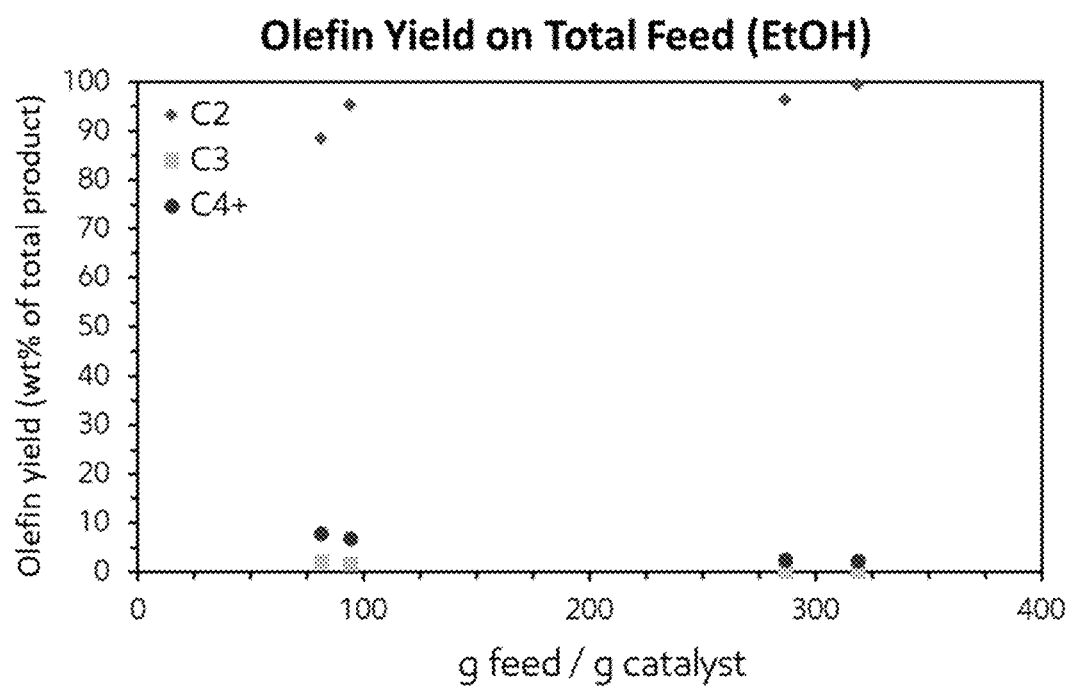
FIG. 16 is a graph showing olefin yields as a percent of the total hydrocarbon product for ZSM-48 at 450° C. utilizing 40% ethanol feed.

Notably, this conversion to olefins occurred despite the presence of a significant amount of water. The results in FIGS. 14-16 demonstrate that significant quantities of C3+ olefins can be produced, especially at lower temperatures.

At 300° C., C3+ olefin yields were quite high, being >25% of the total product, while ethylene yield was ~3% at the beginning of the run. After some time, this changed to primarily ethylene production, but C3+ olefin production remained high for the first 100 g feed/g catalyst of the run. This demonstrates that it is possible to create a significant advantage in the process conditions and energy input requirements for bioethanol conversion.

While not quite as high in C3+ olefins production at 350° C., their production remained steady in the 10-20 wt. % range over the course of the experiment, again indicating the potential long-term operation of a moving bed unit for ethanol conversion to olefins. At 450° C., the C3+ olefin yields were quite low (<10%), decreasing to very low after some time on stream.

Example 5: Conversion of Iso-Propanol to Olefins with ZSM-48

A sample of ZSM-48 was tested in the conversion of iso-propanol to olefins.

Iso-propanol conversion experiments were performed in a ~10 cc reactor, with a fixed bed of ~2 g zeolite catalyst diluted in sand. Iso-propanol feed rate was 5 cc/h and the WHSV was ~2.

The catalyst was contacted with iso-propanol in the fixed bed reactor operating at 450° C. and at a pressure of about 15 psig. The iso-propanol was fed to the zeolite catalyst bed and the effluent from the reactor was periodically analyzed for product composition.

Gas phase analysis was performed with an online GC. The liquid products were separated by density into aqueous and hydrocarbon components. The aqueous phase was analyzed by density measurement and the hydrocarbon phase was analyzed by GC.

Figure 17:
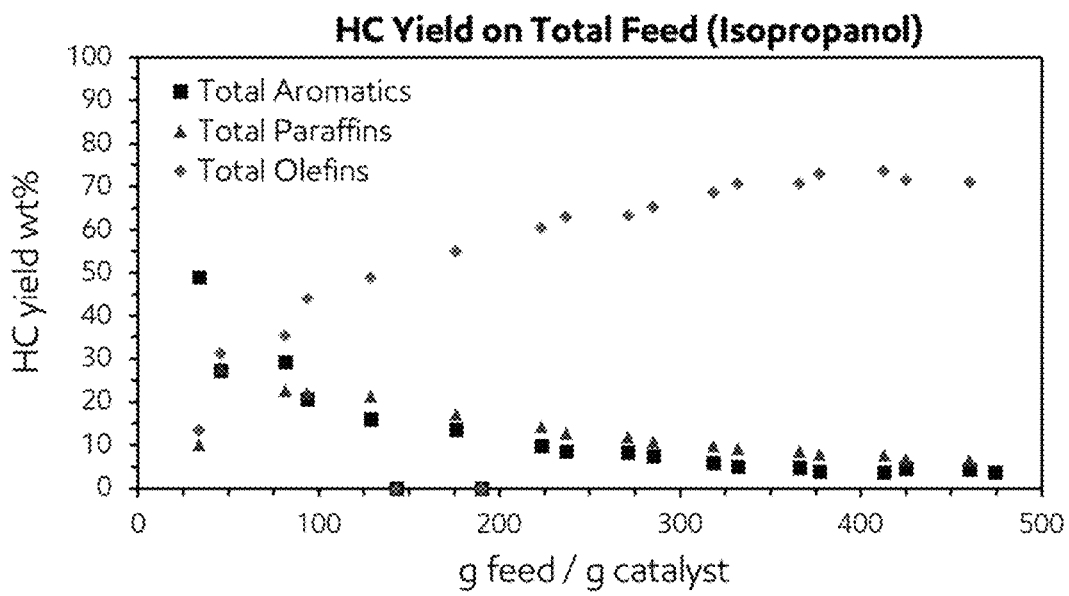
FIG. 17 is a graph showing total hydrocarbon (HC) yields for aromatics, paraffins, and olefins over ZSM-48 at 450° C. utilizing iso-propanol feed.
Figure 18:
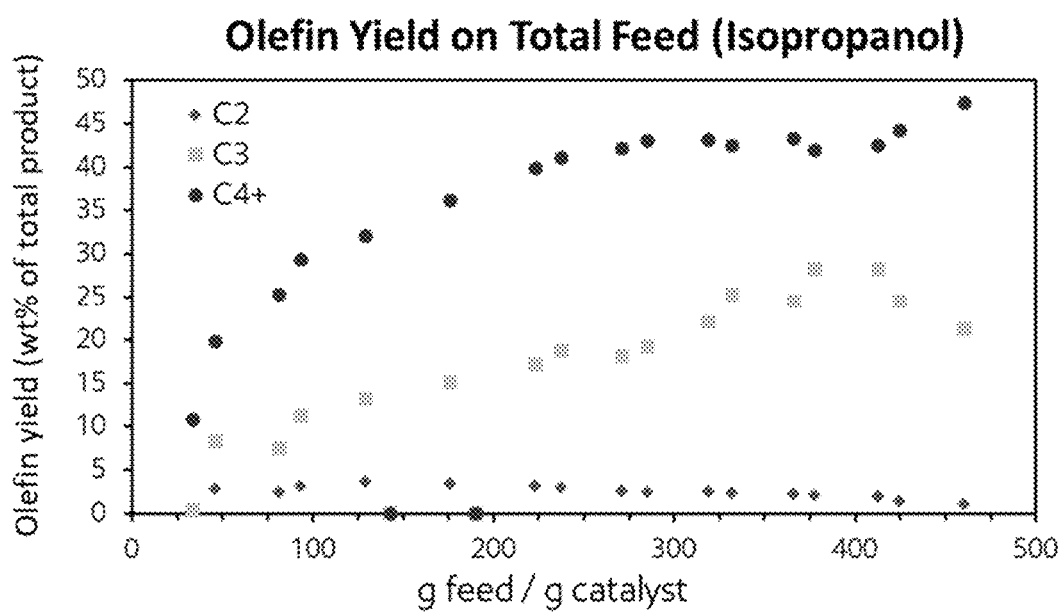
FIG. 18 is a graph showing olefin yields as a percent of the total hydrocarbon product for ZSM-48 at 450° C. utilizing iso-propanol feed.
Figure 19:
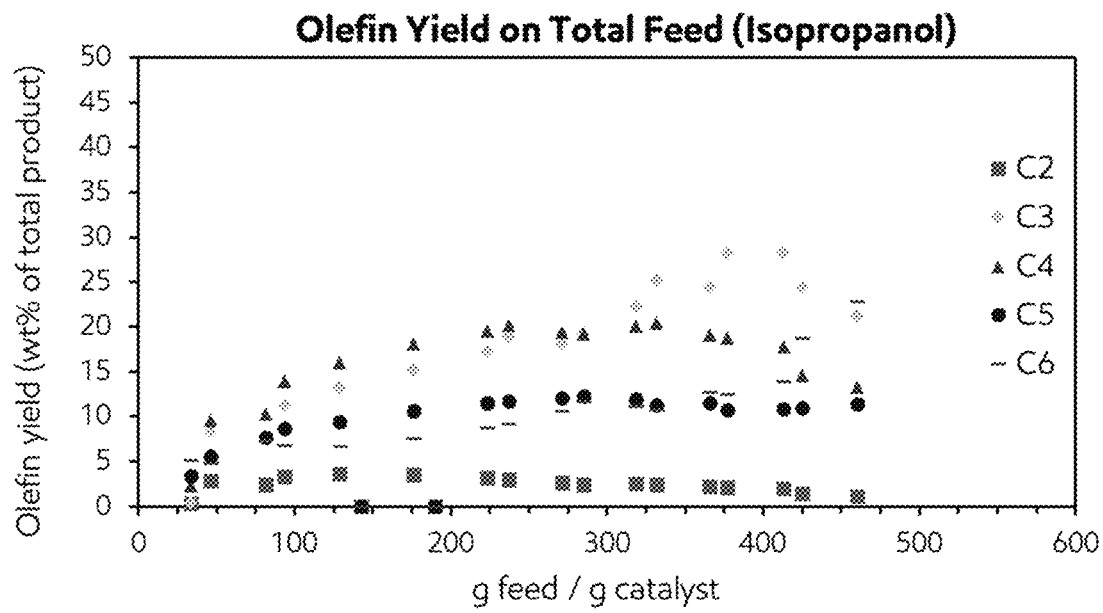
FIG. 19 is a graph showing further detail on olefin yields as a percent of the total hydrocarbon product for ZSM-48 at 450° C. utilizing iso-propanol feed.

FIG. 17 illustrates the weight % hydrocarbon yield against gram iso-propanol feed per gram catalyst (g/g), FIG. 18 the olefin yields at 450° C. and FIG. 19 the detailed olefin distribution.

Referring to FIG. 17, aromatics and paraffins were initially the dominant products, with olefins becoming the dominant product after extended time on stream, at both the expense of paraffins and aromatics. Isopropanol conversion was >99% throughout the run for all mass balances, as, at a minimum, dehydration to propylene was facile, although the results demonstrate that many higher olefinic products were formed as illustrated in FIG. 18.

Higher olefins (C3+) are more desired for subsequent converting to higher value molecules, due to the relative ease of oligomerizing these olefins as compared to ethylene. It is evident that the primary olefinic products from this reaction are C3+, leading to the conclusion that the ZSM-48 catalyst can produce advantaged olefins from an isopropanol feed. This is an important point, as most catalysts for converting propanols to olefins rely on dehydration of the propanol, resulting in a feed of primarily propylene, whereas with this zeolite, many higher olefins (C4-C6) were co-produced along with propylene (FIG. 19). It was observed that the catalyst increased the percentage of C4+ olefins in the products with time on stream.

Example 6: Conversion of 1-Butanol to Olefins with ZSM-48

A sample ZSM-48 was tested in the conversion of 1-butanol to olefins.

1-Butanol conversion experiments were performed in a ~10 cc reactor, with a fixed bed of ~2 g zeolite catalyst diluted in sand. 1-butanol feed rate was 5 cc/h and the WHSV was ~2.

The catalyst was contacted with 1-butanol in the fixed bed reactor operating at 450° C. and at a pressure of about 15 psig. The 1-butanol was fed to the zeolite catalyst bed and the effluent from the reactor was periodically analyzed for product composition.

Gas phase analysis was performed with an online GC. The liquid products were separated by density into aqueous and hydrocarbon components. The aqueous phase was analyzed by density measurement and the hydrocarbon phase was analyzed by GC.

Figure 20:
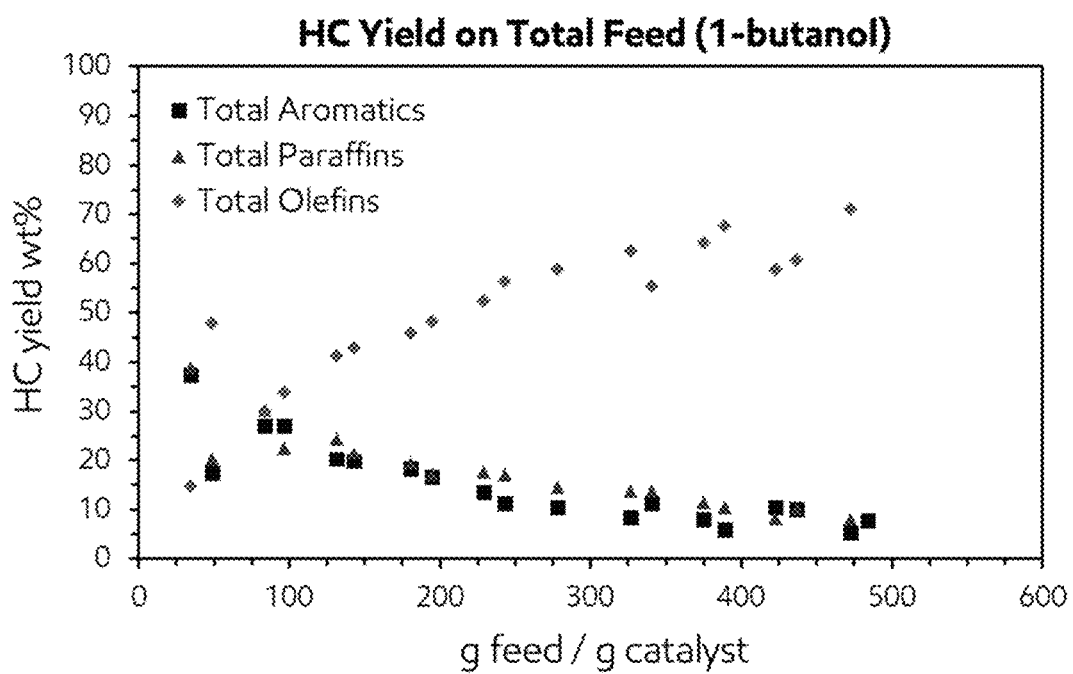
FIG. 20 is a graph showing total hydrocarbon (HC) yields for aromatics, paraffins, and olefins over ZSM-48 at 450° C. utilizing 1-butanol feed.

FIG. 20 illustrates the weight % hydrocarbon yield against gram 1-butanol feed per gram catalyst (g/g). The results indicate that olefins production from the conversion of 1-butanol dominates, with >60 wt. % olefins production among all hydrocarbon products and up to 70 wt. % toward the end of the run.

Figure 21:
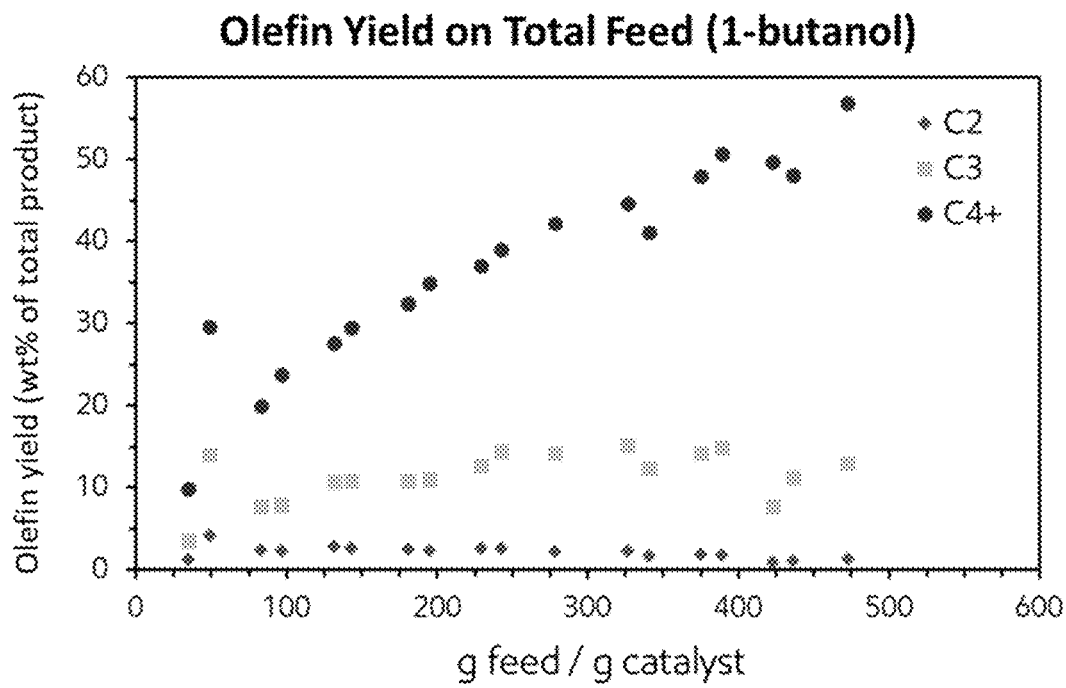
FIG. 21 is a graph showing olefin yields as a percent of the total hydrocarbon product for ZSM-48 at 450° C. utilizing 1-butanol feed.
Figure 22:
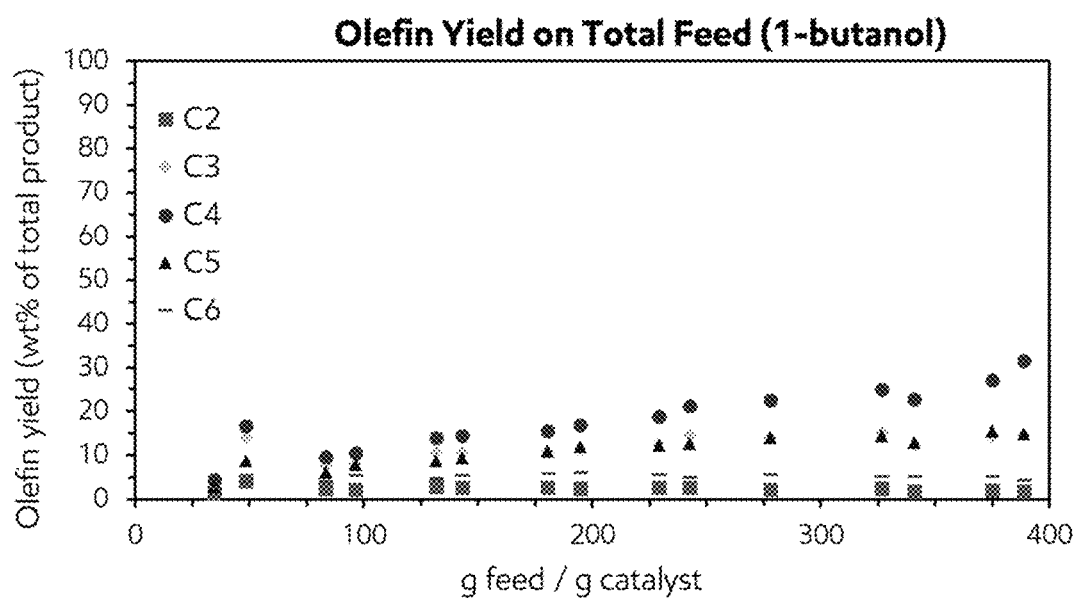
FIG. 22 is a graph showing further detail on olefin yields as a percent of the total hydrocarbon product for ZSM-48 at 450° C. utilizing 1-butanol feed.

Referring to FIG. 21, the production of C4+ olefins at 450° C. continued to rise throughout the run. These olefins are the most desirable for subsequent oligomerization to valuable fuels molecules. Examining the breakdown of olefins (FIG. 22) in more detail, it is evident that butenes were the primary olefinic product, giving 20-30 wt. % of the overall product. This may be expected given that 1-butanol already has a C4 unit in it and simple dehydration yields 1-butene and other butene isomers. However, pentenes were also produced in significant quantities (10-15 wt. %). Ethylene production remained low, which is desirable for an olefin oligomerization feedstock to higher value products.

Figure 23:
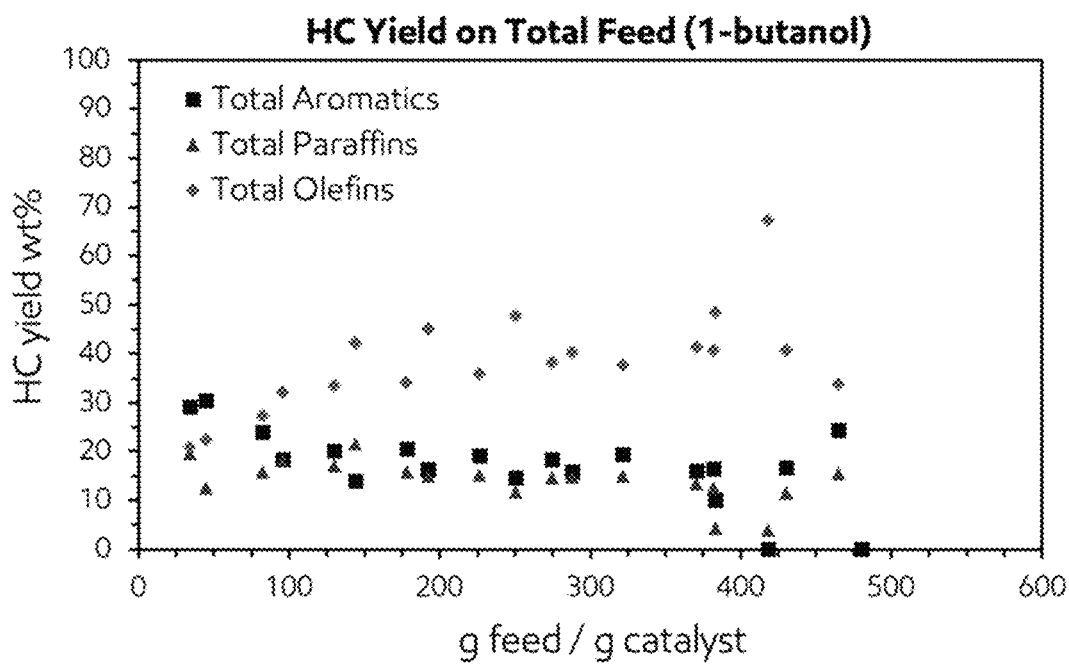
FIG. 23 is a graph showing total hydrocarbon (HC) yields for aromatics, paraffins, and olefins over ZSM-48 at 350° C. utilizing 1-butanol feed.
Figure 24:
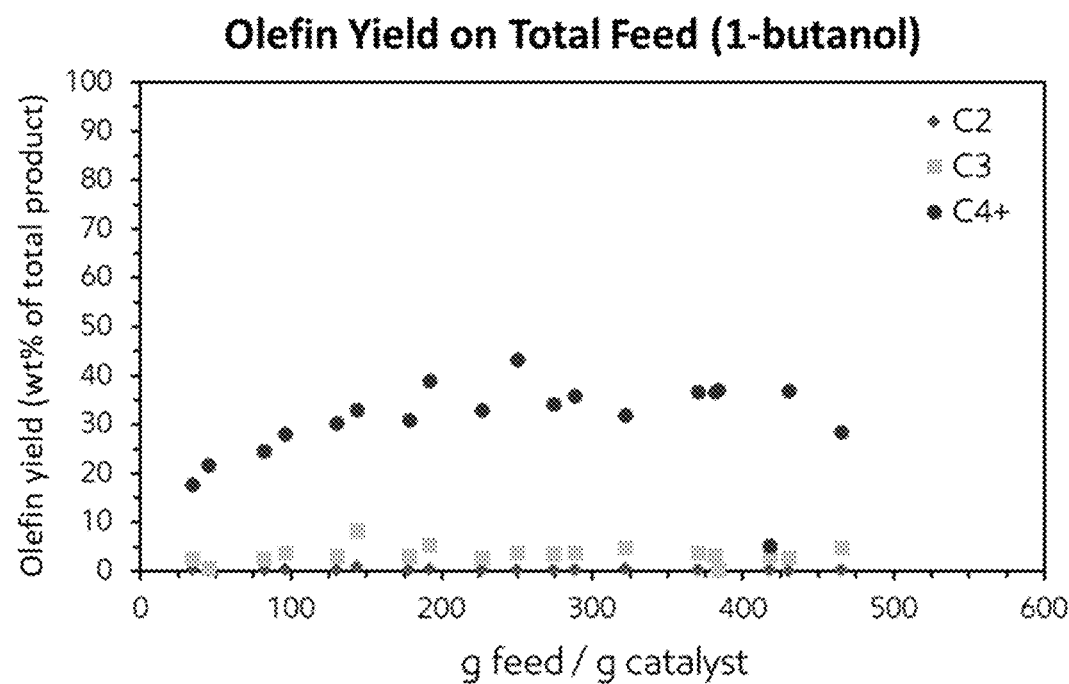
FIG. 24 is a graph showing olefin yields as a percent of the total hydrocarbon product for ZSM-48 at 350° C. utilizing 1-butanol feed.
Figure 25:
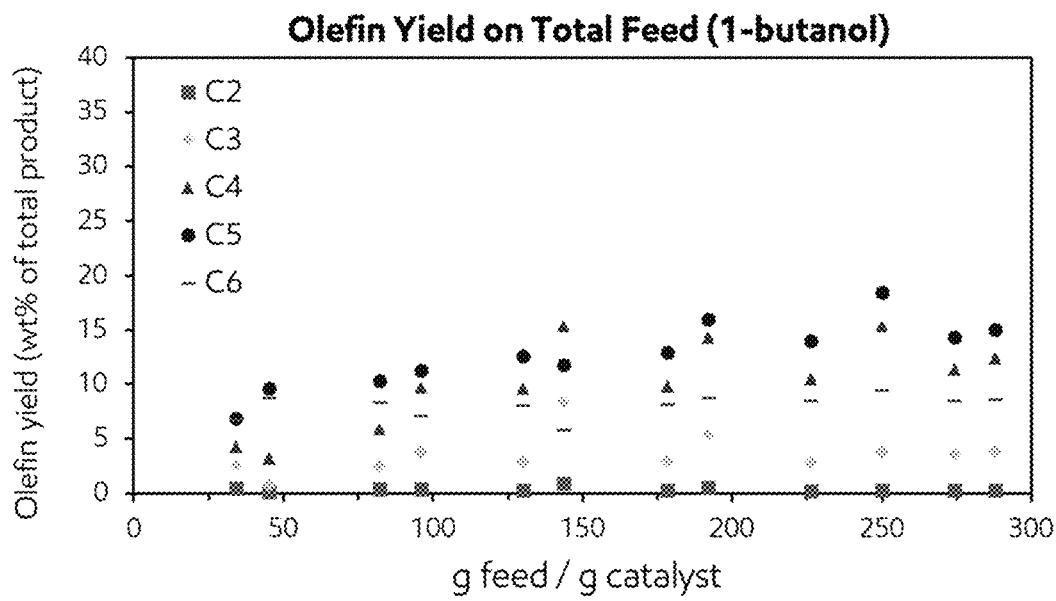
FIG. 25 is a graph showing further detail on olefin yields as a percent of the total hydrocarbon product for ZSM-48 at 350° C. utilizing 1-butanol feed.

Additional experiments were performed with ZSM-48 catalyst and 1-butanol at 350° C. and the resulting data is presented in FIGS. 23-25. FIG. 23 illustrates that olefin production continued to dominate the product mix, with C4+ olefins as 30-40 wt. % of the total products (FIG. 24). Interestingly, the lower temperature resulted in a greater mix of higher olefins, with pentenes being produced in larger quantities than butenes (FIG. 25) despite the starting C4 unit in 1-butanol.

Example 7: Conversion of Iso-Butanol to Olefins with ZSM-48

A sample of ZSM-48 was tested in the conversion of iso-butanol to olefins.

Iso-butanol conversion experiments were performed in a ~10 cc reactor, with a fixed bed of ~2 g zeolite catalyst diluted in sand. Iso-butanol feed rate was 5 cc/h and the WHSV was ~2.

The catalyst was contacted with iso-butanol in the fixed bed reactor operating at 450° C. and at a pressure of about 15 psig. The iso-butanol was fed to the zeolite catalyst bed and the effluent from the reactor was periodically analyzed for product composition.

Gas phase analysis was performed with an online GC. The liquid products were separated by density into aqueous and hydrocarbon components. The aqueous phase was analyzed by density measurement and the hydrocarbon phase was analyzed by GC.

Figure 26:
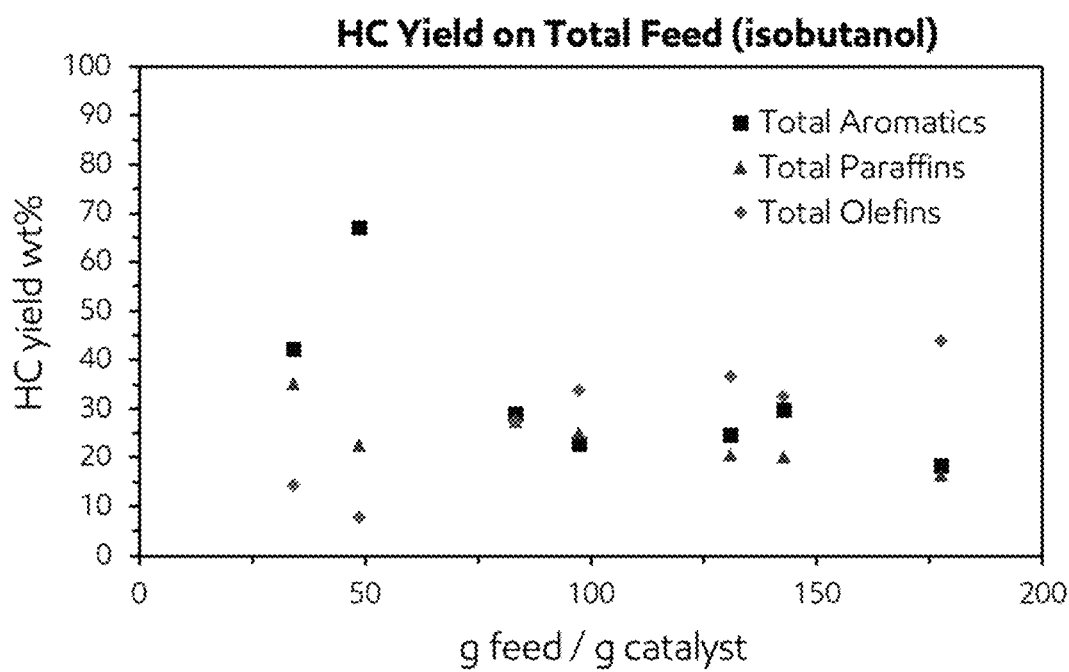
FIG. 26 is a graph showing total hydrocarbon (HC) yields for aromatics, paraffins, and olefins over ZSM-48 at 450° C. utilizing iso-butanol feed.
Figure 27:
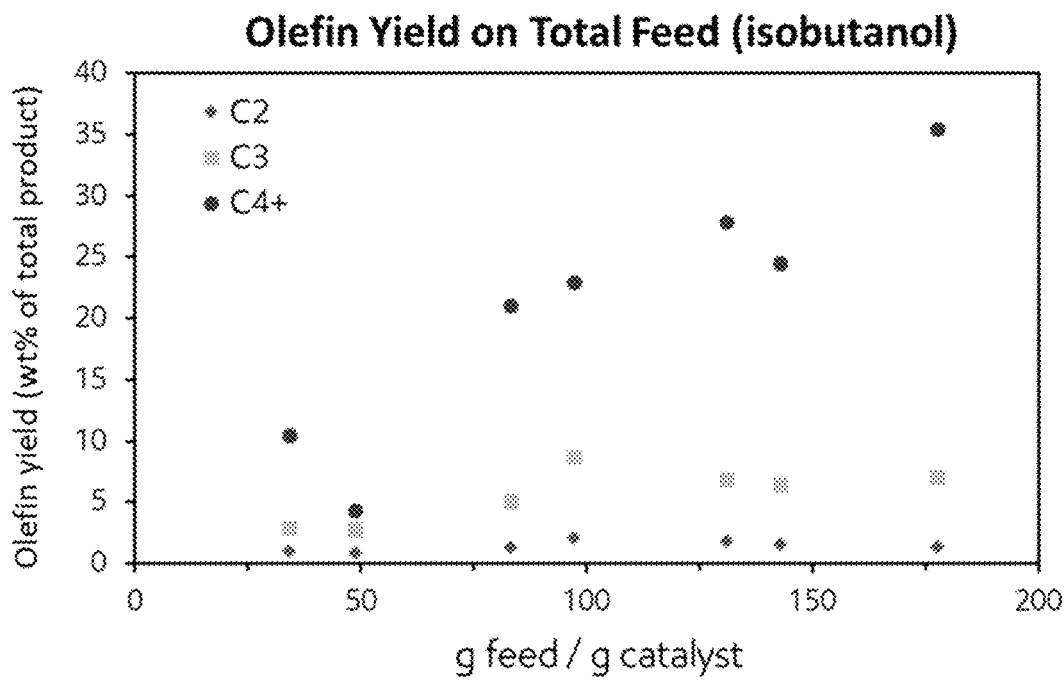
FIG. 27 is a graph showing olefin yields as a percent of the total hydrocarbon product for ZSM-48 at 450° C. utilizing iso-butanol feed.

FIG. 26 illustrates the weight % hydrocarbon yield against gram iso-butanol feed per gram catalyst (g/g). The isobutanol feed significantly changed the product mix, but still produced a large percentage (35%) of higher olefins as products (FIG. 27).

Example 8: Conversion of 1-Butanol to Olefins with 0.5% Zn ZSM-48

A sample of ZSM-48 with 0.5% Zn by weight prepared as in Example 1, was tested to determine the extent to which metal loading impacts the conversion of 1-butanol to olefins.

Figure 28:
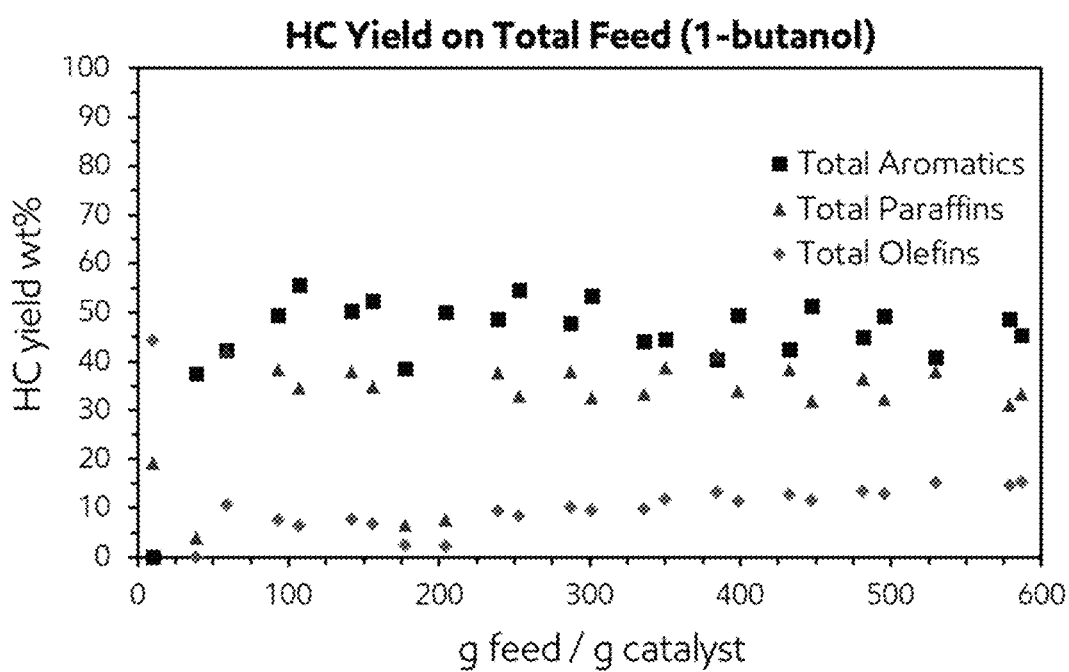
FIG. 28 is a graph showing total hydrocarbon (HC) yields for aromatics, paraffins, and olefins over 0.5% Zn/ZSM-48 at 450° C. utilizing 1-butanol feed.

Referring to FIG. 28, throughout the experiment, aromatics accounted for about 50% of the products. A mass balance indicated that the conversion of 1-butanol was relatively complete, as it was not in the aqueous layer (based on the density of 1.00 g/cm3), and it was also not found in significant quantities in the products (given the mass balance closures of the total aromatics, paraffins, and olefins).

Figure 29:
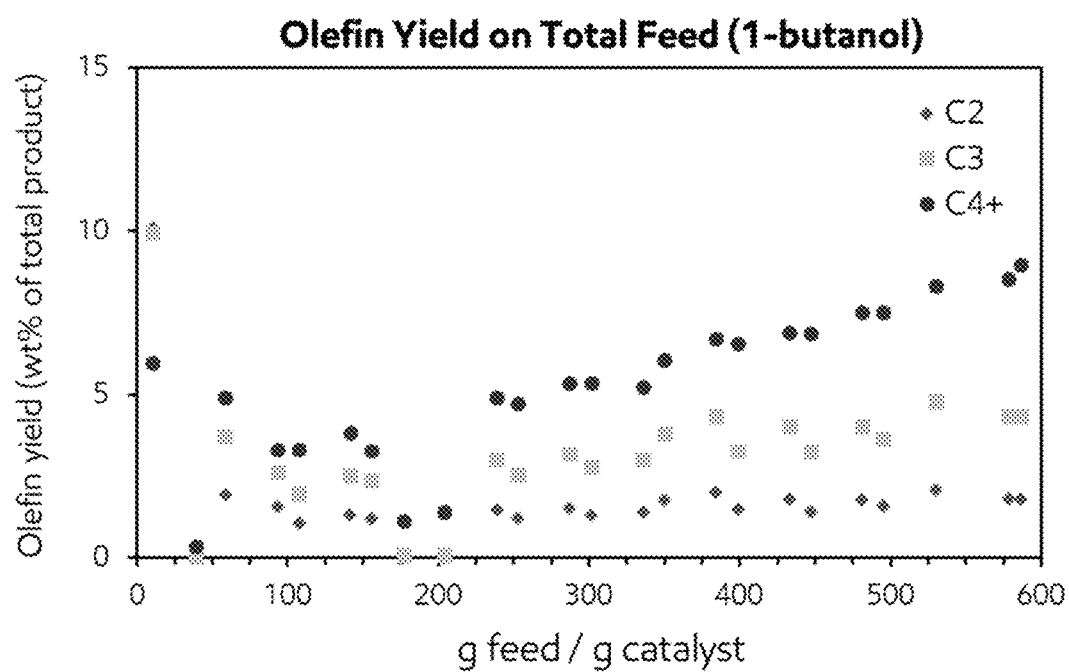
FIG. 29 is a graph showing olefin yields as a percent of the total hydrocarbon product for 0.5% Zn/ZSM-48 at 450° C. utilizing 1-butanol feed.

Examining the distribution of olefinic products can give some insight into the nature of the process occurring during the reaction of 1-butanol (FIG. 29). While the overall percentages of olefins were not particularly high, the C4+ olefin percentages were quite high compared to lower olefins, especially as the catalyst was exposed to more feed. This preference for higher olefins is likely the result of the 1-butanol containing a C4 unit. Cracking is required to produce ethylene and propylene, resulting in their reduced production relative to higher olefins.

Certain Embodiments

Certain embodiments of processes according to the present disclosure are presented in the following paragraphs.

Embodiment 1 provides a process for converting alcohols and/or ethers to olefins, said process comprising: contacting a feed comprising one or more alcohols and/or one or more ethers with a conversion catalyst in a reaction zone at a temperature from about 200° C. to about 550° C. under conditions effective to produce an olefin-containing effluent, the olefin-containing effluent comprising 40 wt. % or more of olefins and 30 wt. % or less of aromatics relative to a weight of hydrocarbons in the olefin-containing effluent, the conversion catalyst comprising a zeolite framework structure.

Embodiment 2 provides a process according to embodiment 1, wherein the wt. % of olefins relative to the weight of hydrocarbons in the olefin-containing effluent is 45 wt. % or more, or 50 wt. % or more, or 55 wt. % or more, or 60 wt. % or more, or 65 wt. % or more, or 70 wt. % or more, or 75 wt. % or more, or 80 wt. % or more, or 85 wt. % or more.

Embodiment 3 provides a process according to embodiment 1 or embodiment 2, wherein the wt. % of aromatics relative to the weight of hydrocarbons in the olefin-containing effluent is 20 wt. % or less, or 15 wt. % or less, or 10 wt. % or less, or 5 wt. % or less.

Embodiment 4 provides a process according to any one of embodiments 1 to 3, wherein the wt. % of C3+ olefins relative to the weight of hydrocarbons in the olefin-containing effluent is 5 wt. % or more, or 10 wt. % or more, or 15 wt. % or more, or 20 wt. % or more, or 25 wt. % or more, or 30 wt. % or more, or 35 wt. % or more.

Embodiment 5 provides a process according to any one of embodiments 1 to 4, wherein the wt. % of C4+ olefins relative to the weight of hydrocarbons in the olefin-containing effluent is 5 wt. % or more, or 10 wt. % or more, or 15 wt. % or more, or 20 wt. % or more, or 25 wt. % or more, or 30 wt. % or more, or 35 wt. % or more.

Embodiment 6 provides a process according to any one of embodiments 1 to 5, wherein the wt. % of paraffins relative to the weight of hydrocarbons in the olefin-containing effluent is 45 wt. % or less, or 40 wt. % or less, or 35 wt. % or less, or 30 wt. % or less, or 25 wt. % or less, or 20 wt. % or less, or 15 wt. % or less, or 10 wt. % or less.

Embodiment 7 provides a process according to any one of embodiments 1 to 6, wherein the wt. % of ethylene relative to the weight of hydrocarbons in the olefin-containing effluent is 50 wt. % or more, or 60 wt. % or more, or 70 wt. % or more, or 80 wt. % or more, or 90 wt. % or more, or 95 wt. % or more.

Embodiment 8 provides a process according to any one of embodiments 1 to 7, wherein the contacting occurs at a temperature from about 250° C. to about 550° C.

Embodiment 9 provides a process according to any one of embodiments 1 to 8, wherein the contacting occurs at a pressure from about 5 psig to about 400 psig.

Embodiment 10 provides a process according to any one of embodiments 1 to 9, wherein the WHSV is from about 0.1 h-1 to about 10 h-1.

Embodiment 11 provides a process according to any one of embodiments 1 to 10, wherein the conversion catalyst comprises a MRE type zeolite.

Embodiment 12 provides a process according to any one of embodiments 1 to 11, wherein the conversion catalyst comprises ZSM-48.

Embodiment 13 provides a process according to any one of embodiments 1 to 12, wherein the conversion catalyst is a self-bound catalyst.

Embodiment 14 provides a process according to any one of embodiments 1 to 12, wherein the conversion catalyst further comprises about 1 wt. % to about 40 wt. % of a binder comprising one or more of Al2O3, TiO2, ZrO2, SiO2, SiO2/Al2O3 and MgO, based on the total weight of the conversion catalyst.

Embodiment 15 provides a process according to any one of embodiments 1 to 14, wherein the conversion catalyst further comprises about 0.1 wt. % to about 20 wt. % of one or more metals selected from groups 1 to 14 of the periodic table.

Embodiment 16 provides a process according to embodiment 15, wherein the one or more metals comprise one or more of Zn, Ga, B, Ca, Ti, V, Fe, Cu, Mo, Ru, Pd, Rh, Ir, Nb, W, Re, and Pt.

Embodiment 17 provides a process according to embodiment 15, wherein the conversion catalyst comprises about 0.1 wt. % to about 20 wt. % of one or more metals selected from groups 12 to 14 of the periodic table.

Embodiment 18 provides a process according to embodiment 15, wherein the conversion catalyst comprises about 0.1 wt. % to about 5 wt. % of one or more metals selected from groups 12 to 14 of the periodic table.

Embodiment 19 provides a process according to embodiment 15, wherein the conversion catalyst comprises Zn.

Embodiment 20 provides a process according to embodiment 19, wherein the conversion catalyst comprises about 0.1 wt. % to about 2 wt. % Zn.

Embodiment 21 provides a process according to any one of embodiments 1 to 20, wherein the reaction zone comprises one or more of a fixed bed reactor, a fluidized bed reactor, a riser reactor, and a moving bed reactor.

Embodiment 22 provides a process according to any one of embodiments 1 to 21, wherein the reaction zone comprises one or more moving bed reactors.

Embodiment 23 provides a process according to embodiment 21 or embodiment 22, further comprising a step of transferring at least a portion of the conversion catalyst to a regeneration zone, separate from the reaction zone, and contacting the conversion catalyst with a regeneration gas in the regeneration zone to at least partially remove coke deposited on the conversion catalyst in the reaction zone, whereby the conversion catalyst is at least partially regenerated, and then returning the thus at least partially regenerated conversion catalyst to the reaction zone.

Embodiment 24 provides a process according to embodiment 23, wherein the regeneration gas comprises oxygen, for example, air.

Embodiment 25 provides a process according to embodiment 23 or embodiment 24, wherein the at least partially regenerated conversion catalyst is returned to the reaction zone at a rate sufficient to produce an olefin-containing effluent comprising 5 wt. % or more of C3+ olefins, relative the weight of hydrocarbons in the olefin-containing effluent Embodiment 26 provides a process according to any one of embodiments 23 to 25, wherein the at least partially regenerated conversion catalyst is returned to the reaction zone at a rate sufficient to produce an olefin-containing effluent comprising 10 wt. % or more of C3+ olefins, or 15 wt. % or more, or 20 wt. % or more, or 25 wt. % or more, or 30 wt. % or more, or 35 wt. % or more, relative the weight of hydrocarbons in the olefin-containing effluent.

Embodiment 27 provides a process according to any one of embodiments 23 to 26, wherein the at least partially regenerated conversion catalyst is returned to the reaction zone at a rate sufficient such that 1 gram of conversion catalyst is, on average, exposed to at least 200 gram of feed in the reaction zone.

Embodiment 28 provides a process according to any one of embodiments 23 to 27, wherein the at least partially regenerated conversion catalyst is returned to the reaction zone at a rate sufficient such that 1 gram of conversion catalyst is, on average, exposed to at least 300 gram of feed, or at least 400 gram of feed, or at least 500 gram of feed in the reaction zone.

Embodiment 29 provides a process according to any one of embodiments 23 to 26, wherein the at least partially regenerated conversion catalyst is returned to the reaction zone at a rate sufficient such that 1 gram of conversion catalyst is, on average, exposed to no more than 200 gram of feed in the reaction zone.

Embodiment 30 provides a process according to any one of embodiments 23 to 26, wherein the at least partially regenerated conversion catalyst is returned to the reaction zone at a rate sufficient such that 1 gram of conversion catalyst is, on average, exposed to no more than 150 gram of feed, or no more than 100 gram of feed, or no more than 50 gram of feed in the reaction zone.

Embodiment 31 provides a process according to any one of embodiments 23 to 30, wherein the at least partially regenerated conversion catalyst is returned to the reaction zone at a rate sufficient to afford an average degree of conversion catalyst coking within the reaction zone to produce an olefin-containing effluent comprising 5 wt. % or more of C3+ olefins, relative the weight of hydrocarbons in the olefin-containing effluent.

Embodiment 32 provides a process according to any one of embodiments 23 to 31, wherein the at least partially regenerated conversion catalyst is returned to the reaction zone at a rate sufficient to afford an average degree of conversion catalyst coking within the reaction zone to produce an olefin-containing effluent comprising 10 wt. % or more of C3+ olefins, or 15 wt. % or more, or 20 wt. % or more, or 25 wt. % or more, or 30 wt. % or more, or 35 wt. % or more, relative the weight of hydrocarbons in the olefin-containing effluent.

Embodiment 33 provides a process according to any one of embodiments 23 to 32, wherein the at least partially regenerated conversion catalyst is returned to the reaction zone at a rate sufficient to produce an olefin-containing effluent comprising 50 wt. % or more of ethylene, relative the weight of hydrocarbons in the olefin-containing effluent Embodiment 34 provides a process according to any one of embodiments 23 to 33, wherein the at least partially regenerated conversion catalyst is returned to the reaction zone at a rate sufficient to produce an olefin-containing effluent comprising 60 wt. % or more of ethylene, or 70 wt. % or more, or 80 wt. % or more, or 90 wt. % or more, or 95 wt. % or more, relative the weight of hydrocarbons in the olefin-containing effluent.

Embodiment 35 provides a process according to any one of embodiments 23 to 34, wherein the at least partially regenerated conversion catalyst is returned to the reaction zone at a rate sufficient to afford an average degree of conversion catalyst coking within the reaction zone to produce an olefin-containing effluent comprising 50 wt. % or more of ethylene, relative the weight of hydrocarbons in the olefin-containing effluent.

Embodiment 36 provides a process according to any one of embodiments 23 to 35, wherein the at least partially regenerated conversion catalyst is returned to the reaction zone at a rate sufficient to afford an average degree of conversion catalyst coking within the reaction zone to produce an olefin-containing effluent comprising 60 wt. % or more of ethylene, or 70 wt. % or more, or 80 wt. % or more, or 90 wt. % or more, or 95 wt. % or more, relative the weight of hydrocarbons in the olefin-containing effluent.

Embodiment 37 provides a process according to any one of embodiments 23 to 36, wherein the regeneration zone is a riser reactor, a moving bed reactor or fixed bed reactor.

Embodiment 38 provides a process according to any one of embodiments 1 to 37, wherein the one or more alcohols comprise one or more of ethanol, 1-propanol, 2-propanol, 1-butanol and 2-butanol.

Embodiment 39 provides a process according to any one of embodiments 1 to 38, wherein the one or more alcohols are derived from fermentation or bio-conversion.

Embodiment 40 provides a process according to any one of embodiments 1 to 39, wherein the feed comprising one or more alcohols comprises at least 5% by weight of the one or more alcohols.

Embodiment 41 provides a process according to any one of embodiments 1 to 40, wherein the feed comprising one or more alcohols further comprises water.

Embodiment 42 provides a process according to any one of embodiments 1 to 37, wherein the one or more ethers comprise one or more of diethyl ether, di-n-propyl ether, di-iso-propyl ether, di-n-butyl ether and di-iso-butyl ether.

Embodiment 43 provides a process according to any one of embodiments 1 to 42, further comprising the step of separating water from the olefin-containing effluent.

Embodiment 44 provides a process according to any one of embodiments 1 to 43, further comprising the step of separating at least some of the olefin-containing effluent to provide a stream rich in olefins.

Embodiment 45 provides a process according to embodiment 44, further comprising the step of separating at least some of the stream rich in olefins to provide at least a stream rich in ethylene and a stream rich in C3+ olefins.

Embodiment 46 provides a process according to embodiments 45, wherein the stream rich in ethylene is further oligomerized.

Embodiment 47 provides a process according to embodiment 45, wherein at least some of the C3+ olefins are oligomerized to higher olefins.

Embodiment 48 provides a process according to embodiments 47, wherein at least some of the higher olefins are hydrogenated to jet or diesel fuels.

The contents of all references and published patents and patent applications cited throughout the application are hereby incorporated by reference.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A process for converting alcohols and/or ethers to olefins, said process comprising:
contacting a feed comprising one or more alcohols and/or one or more ethers with a conversion catalyst in a reaction zone at a temperature from about 200° C. to about 550° C. under conditions effective to produce an olefin-containing effluent, the olefin-containing effluent comprising 5 wt.% or more of C3+ olefins, 40 wt.% or more of olefins and 30 wt.% or less of aromatics relative to a weight of hydrocarbons in the olefin-containing effluent, the conversion catalyst comprising a zeolite selected from at least one of MRE or ZSM-48, wherein the zeolite comprises 0.1 to 2 wt.% Zn.

2. A process according to claim 1, wherein the wt.% of olefins relative to the weight of hydrocarbons in the olefin-containing effluent is 45 wt.% or more.

3. A process according to claim 1, wherein the wt.% of aromatics relative to the weight of hydrocarbons in the olefin-containing effluent is 20 wt.% or less.

4. A process according to claim 1, wherein a wt.% of C4+ olefins relative to the weight of hydrocarbons in the olefin-containing effluent is 5 wt.% or more.

5. A process according to claim 1, wherein a wt.% of paraffins relative to the weight of hydrocarbons in the olefin-containing effluent is 45 wt.% or less.

6. A process according to claim 1, wherein a wt.% of ethylene relative to the weight of hydrocarbons in the olefin-containing effluent is 50 wt.% or more.

7. A process according to claim 1, wherein the contacting occurs at a temperature from about 250° C. to about 550° C.

8. A process according to claim 1, wherein the contacting occurs at a pressure from about 5 psig to about 400 psig.

9. A process according to claim 1, wherein the WHSV is from about 0.1 h$^{-1}$ to about 10 h$^{-1}$.

10. A process according to claim 1, wherein the conversion catalyst is a self-bound catalyst.

11. A process according to claim 1, wherein the conversion catalyst further comprises about 1 wt.% to about 40 wt.% of a binder comprising one or more of $Al_2O_3$, $TiO_2$, $ZrO_2$, $SiO_2$, $SiO_2/Al_2O_3$ and MgO, based on the total weight of the conversion catalyst.

12. A process according to claim 1, wherein the reaction zone comprises one or more of a fixed bed reactor, a fluidized bed reactor, a riser reactor, and a moving bed reactor.

13. A process according to claim 1, wherein the reaction zone comprises one or more moving bed reactors.

14. A process according to claim 13, further comprising a step of transferring at least a portion of the conversion catalyst to a regeneration zone, separate from the reaction zone, and contacting the conversion catalyst with a regeneration gas in the regeneration zone to at least partially remove coke deposited on the conversion catalyst in the reaction zone, whereby the conversion catalyst is at least partially regenerated, and then returning the thus at least partially regenerated conversion catalyst to the reaction zone.

15. A process according to claim 14, wherein the at least partially regenerated conversion catalyst is returned to the reaction zone at a rate sufficient to produce an olefin-containing effluent comprising 5 wt.% or more of C3+ olefins, relative the weight of hydrocarbons in the olefin-containing effluent.

16. A process according to claim 14, wherein the at least partially regenerated conversion catalyst is returned to the reaction zone at a rate sufficient such that 1 gram of conversion catalyst is, on average, exposed to at least 200 gram of feed in the reaction zone.

17. A process according to claim 14, wherein the at least partially regenerated conversion catalyst is returned to the reaction zone at a rate sufficient such that 1 gram of conversion catalyst is, on average, exposed to no more than 200 gram of feed in the reaction zone.

18. A process according to claim 14, wherein the at least partially regenerated conversion catalyst is returned to the reaction zone at a rate sufficient to afford an average degree of conversion catalyst coking within the reaction zone to produce an olefin- containing effluent comprising 5 wt.% or more of C3+ olefins, relative the weight of hydrocarbons in the olefin-containing effluent.

19. A process according to claim 14, wherein the at least partially regenerated conversion catalyst is returned to the reaction zone at a rate sufficient to produce an olefin-containing effluent comprising 50 wt.% or more of ethylene, relative the weight of hydrocarbons in the olefin-containing effluent.

20. A process according to claim 14, wherein the at least partially regenerated conversion catalyst is returned to the reaction zone at a rate sufficient to afford an average degree of conversion catalyst coking within the reaction zone to produce an olefin- containing effluent comprising 50 wt.% or more of ethylene, relative the weight of hydrocarbons in the olefin-containing effluent.

21. A process according to claim 14, wherein the regeneration zone is a riser reactor, a moving bed reactor or fixed bed reactor.

22. A process according to claim 1, wherein the one or more alcohols comprise one or more of ethanol, 1-propanol, 2-propanol, 1-butanol and 2-butanol.

23. A process according to claim 1, wherein the olefin-containing effluent further comprises paraffins and water, and wherein the process further comprises:
introducing the olefin-containing effluent into a first separator and separating at least a portion of the olefin-containing effluent to form a water stream comprising at least a portion of the water from the olefin-containing effluent, and a hydrocarbon stream comprising at least a portion of the olefins, the aromatics, and the paraffins;
introducing the hydrocarbon stream into a second separator and separating at least a portion of the hydrocarbon stream to form a bottoms stream comprising at least a portion of the olefins and the aromatics from the hydrocarbon stream and an stream comprising olefins comprising at least a portion of the olefins from the hydrocarbon stream, wherein the stream comprising olefins comprises ethylene and C3+ olefins;
introducing the stream comprising olefins into a third separator and separating at least a portion of the olefin rich stream to form an ethylene stream comprising at least a portion of the ethylene from the olefin rich stream and a C3+ olefin stream comprising the C3+ olefins from the olefin rich stream; and
introducing the C3+ olefin stream into an oligomerization reactor and oligomerizing at least a portion of the olefins in the C3+ olefin stream to form an oligomerized stream.

24. A process according to claim 23, further comprising:
introducing the oligomerized stream into a hydrogenator and hydrogenating at least a portion of the oligomerized stream.

25. The process according to claim 1, wherein the zeolite comprises about 0.5 wt.% Zn.

* * * * *